US007727744B2

(12) United States Patent
Fiandt et al.

(10) Patent No.: US 7,727,744 B2
(45) Date of Patent: Jun. 1, 2010

(54) METHODS FOR OBTAINING DIRECTIONALLY TRUNCATED POLYPEPTIDES

(75) Inventors: Michael J. Fiandt, Cambridge, WI (US); Gary A. Dahl, Madison, WI (US)

(73) Assignee: Epicentre Technologies Corporation, Madison, WI (US)

( * ) Notice: Subject to any disclaimer, the term of this patent is extended or adjusted under 35 U.S.C. 154(b) by 642 days.

(21) Appl. No.: 11/093,387

(22) Filed: Mar. 30, 2005

(65) Prior Publication Data

US 2006/0014169 A1 Jan. 19, 2006

Related U.S. Application Data

(60) Provisional application No. 60/521,313, filed on Mar. 30, 2004, provisional application No. 60/572,446, filed on May 19, 2004.

(51) Int. Cl.
*C12P 21/02* (2006.01)
*C12P 21/06* (2006.01)
*C12N 15/64* (2006.01)
*C12N 15/00* (2006.01)

(52) U.S. Cl. .................. 435/70.1; 435/69.1; 435/91.41; 435/455

(58) Field of Classification Search ........................ None
See application file for complete search history.

(56) References Cited

U.S. PATENT DOCUMENTS

| | | | |
|---|---|---|---|
| 4,843,003 | A | 6/1989 | Henikoff et al. |
| 5,356,773 | A | 10/1994 | Shen et al. |
| 5,677,170 | A | 10/1997 | Devine et al. |
| 5,728,551 | A | 3/1998 | Devine et al. |
| 5,733,753 | A | 3/1998 | Jørgensen |
| 5,928,908 | A | 7/1999 | Dunn et al. |
| 5,948,622 | A | 9/1999 | Reznikoff et al. |
| 5,968,768 | A | 10/1999 | Haynes et al. |
| 5,968,785 | A | 10/1999 | Devine et al. |
| 6,159,736 | A | 12/2000 | Reznikoff et al. |
| 6,248,569 | B1 | 6/2001 | Dunn et al. |
| 6,265,159 | B1 | 7/2001 | Sugino et al. |
| 6,294,385 | B1 | 9/2001 | Goryshin et al. |
| 6,504,081 | B1 | 1/2003 | Westphal et al. |
| 6,593,113 | B1 | 7/2003 | Tenkanen et al. |
| 2003/0096349 | A1 | 5/2003 | Kazmierczak et al. |

FOREIGN PATENT DOCUMENTS

| | | |
|---|---|---|
| WO | WO 95/23875 | 9/1995 |
| WO | WO 97/29202 | 8/1997 |
| WO | WO98/10077 | 3/1998 |
| WO | WO98/37205 | 8/1998 |
| WO | WO98/40510 | 9/1998 |
| WO | WO 03/087370 | 10/2003 |

OTHER PUBLICATIONS

Brune et al (Rapid Identification of essential and non-essential herpesvirus genes by direct transposon mutagenesis. Nature Biotechnology, 1999. 17:360-364).*
Hobom et al (Fast Screening Procedure for Random Transposon Libraries of Cloned Herpesvirus Genomes: Mutational Analysis of Human Cytomegalovirus Envelope Glycoprotein Genes. Journal of Virology, 2000. 74(17)7720-7729).*
Costa et al (Cloning and analysis of PCR-generated fragments. PCR Methods and Applications, 1994. 3(6): 338-345).*
Yohda et al., Solid-Phase Nested Deletion: A New Subcloning-less Method for Generating Nested Deletions; DNA Research, 2:175-181, (1995).
Zhu and Clarke, Rapid construction of nested deletions of recombinant plasmid DNA for dideoxy sequencing.; BioTechniques, 18:222-224, (1995).
Henikoff et al., Unidirectional digestion with exonuclease III creates targeted breakpoints for DNA sequencing.; Gene, 28:351-359, (1984).
Pues et al., Construction of a deletion library using a mixture of 5'-truncated primers for inverse PCR (IPCR); Nucleic Acids Res. 25:1303-1304, (1997).
Strathmann et al., Transposon-Facilitated DNA Sequencing; Proc. Nat. Acad. Sci. USA 88:1247-1250, (1991).
Phadnis et al., Tn5supF, a 264-Base-Pair Transposon Derived from Tn5 for Insertion Mutagenesis and Sequencing DNAs Cloned in Phage lambda; Proc. Nat. Acad. Sci. USA 86:5908-.
Way et al., New Tn10 derivatives for transposon mutagenesis and for construction of lacZ operon fusions by transposition.; Gene 32:369-279, (1984).
Kleckner et al., Uses of transposons with emphasis on Tn10.; Method. Enzymol. 204:139-180, (1991).
Lee et al., Efficient Tn 10 Transposition into a DNA Insertion Hot Spot in vivo Requires the 5-methyl Groups of Symmetrically Disposed Thymines within the Hot-Spot Consensus Sequence: Proc. Nat. Acad. Sci. USA 84:7876, (1987).

(Continued)

*Primary Examiner*—Michael Burkhart
(74) *Attorney, Agent, or Firm*—Casimir Jones SC

(57) ABSTRACT

Methods, compositions and kits are disclosed for obtaining directionally truncated polypeptides by inserting a transposon. Preferably the transposon comprises a selectable marker and an ori, and optionally a promoter, a ribosome binding site and a translation start codon, into a target sequence in vitro or in vivo. Amplification products, varying in length depending on the transposon insertion site, are obtained using one primer that anneals to the target sequence and a second primer that anneals to the transposon. Amplification products are ligated to circular dsDNA, transformed into host cells, and individual colonies, each containing a directionally truncated clone of the target sequence, are obtained by plating on medium for which the selectable marker encodes resistance. Directionally truncated polypeptides encoded by the target sequence are obtained in vivo by inducing an RNAP in the host cells that uses the promoter or, in vitro by cell-free transcription and translation.

40 Claims, 8 Drawing Sheets

Brown et al., Correct integration of retroviral DNA in vitro.; Cell, 49:347-356, (1987).

Eichinger et al., The DNA intermediate in yeast Ty1 element transposition copurifies with virus-like particles: cell-free Ty1 transposition.; Cell, 54:955-966, (1988).

Eichinger et al., A specific terminal structure is required for Ty1 transposition; Genes Dev., 4:324-330, (1990).

Ahmed, Use of transposon-promoted deletions in DNA sequence analysis.; J. Mol. Biol., 178:941-948, (1984).

Hattori et al., A novel method for making nested deletions and its application for sequencing of a 300 kb region of human APP locus; Nucleic Acids Res. 25:1802-1808, (1997).

Jilk et al., Implications of Tn5-associated adjacent deletions.; J. Bacteriology, 175:1264-1271, (1993).

Krishnan et al., Construction of a genomic DNA 'feature map' by sequencing from nested deletions: application to the HLA class I region; Nucleic Acids Res. 23:117-122, (1995).

Morita et al., Nested Deletions from a Fixed Site as an Aid to Nucleotide Sequencing: an in vitro System Using Tn3 Transposase; DNA Research, 3:431-433, (1996).

Wang et al., pDUAL: A Transposon-Based Cosmid Cloning Vector for Generating Nested Deletions and DNA Sequencing Templates in vivo; Proc. Natl. Acad. Sci., 90:7874-7878, (1993).

York et al., Simple and efficient generation in vitro of nested deletions and inversions: Tn5 intramolecular transposition; Nucleic Acids Res. 26:1927, (1998).

Goryshin, I. and Reznikoff, Tn5 in Vitro Transposition; W.S., J. Biol. Chem., 273:7367, (1998).

Mizuuchi, K., In vitro transposition of bacteriophage Mu: a biochemical approach to a novel replication reaction.; Cell, 35;785, (1983).

Savilahti, H, et al., The phage Mu transpososome core: DNA requirements for assembly and function.; EMBO J., 14:4893, (1995).

Colegio OR et al., In Vitro Transposition System for Efficient Generation of Random Mutants of Campylobacter jejuni; J Bacteriol., 183:2384-8, (2001).

Kirby C et al., Cryptic plasmids of Mycobacterium avium: Tn552 to the rescue.; Mol Microbiol., 43:173-86, (2002).

Devine SE, and Boeke JD., Efficient integration of artificial transposons into plasmid targets in vitro: a useful tool for DNA mapping, sequencing and genetic analysis; Nucleic Acids Res., 22:3765-72, (1994).

Craig, NL, Update: V(D)J Recombination and Transposition: Closer Than Expected; Science. 271:1512, (1996).

Craig, NL, Transposon Tn7.; Curr Top Microbiol Immunol., 204:27-48, (1996).

Kleckner N, et al., Tn10 and IS10 transposition and chromosome rearrangements: mechanism and regulation in vivo and in vitro.; Curr Top Microbiol Immunol., 204:49-82, (1996).

Lampe DJ, et al., A purified mariner transposase is sufficient to mediate transposition in vitro.; EMBO J., 15:5470-9, (1996).

Plasterk RH, The Tc1/mariner transposon family.; Curr Top Microbiol Immunol, 204:125-43, (1996).

Gloor, Gene targeting in *Drosophila*.; Methods Mol Biol., 260:97-114, (2004).

Ichikawa H, and Ohtsubo E., In vitro transposition of transposon Tn3; J Biol Chem. 265:18829-32, (1990).

Ohtsubo, F and Sekine, Y, Bacterial insertion sequences.; Curr. Top. Microbiol. Immunol., 204:1-26, (1996).

Brown et al., Retroviral Integration: Structure of the Initial Covalent Product and Its Precursor, and a Role for the Viral IN Protein; Proc Natl Acad Sci USA, 86:2525-9, (1989).

Boeke JD and Corces VG, Transcription and reverse transcription of retrotransposons.; Annu Rev Microbiol., 43:403-34, (1989).

Dennis JJ and Zylstra GJ, Plasposons: Modular Self-Cloning Minitransposon Derivatives for Rapid Genetic Analysis of Gram-Negative Bacterial Genomes; Appl. Environ. Microbiol. 64:2710-2715, (1998.

Zhou and Doetsch, Effects of Abasic Sites and DNA Single-Strand Breaks on Prokaryotic RNA Polymerases; Proc. Nat. Acad. Sci. USA 90:6601-6605, (1993).

Martin, and Coleman, Kinetic analysis of T7 RNA polymerase-promoter interactions with small synthetic promoters.; Biochemistry 26:2690-2696, (1987).

McGraw et al., Sequence and analysis of the gene for bacteriophage T3 RNA polymerase; Nucl. Acid. Res. 13:6753-6766, (1985).

Kazmierczak et al., The phage N4 virion RNA polymerase catalytic domain is related to single-subunit RNA polymerases.; EMBO J., 21:5815-5823, (2002).

Wang et al., "Inversions and deletions generated by a mini-gamma delta (Tn1000) transposon," Bacteriology, 176:1332-1338, (1994).

* cited by examiner

SEQUENCE LISTING

<160> NUMBER OF SEQ ID NOS: 12

<210> SEQ ID NO 1
<211> LENGTH: 20
<212> TYPE: DNA
<213> ORGANISM: Artificial
<220> FEATURE:
<223> OTHER INFORMATION: Synthetic

<400> SEQUENCE: 1
caggcacgga cattatggtt                                            20

<210> SEQ ID NO 2
<211> LENGTH: 20
<212> TYPE: DNA
<213> ORGANISM: Artificial
<220> FEATURE:
<223> OTHER INFORMATION: Synthetic

<400> SEQUENCE: 2
aggcatgttc aggcgaatct                                            20

<210> SEQ ID NO 3
<211> LENGTH: 24
<212> TYPE: DNA

```
<213> ORGANISM: Artificial
<220> FEATURE:
<223> OTHER INFORMATION: Synthetic

<400> SEQUENCE: 3
agatgtaggt gttccacagg gtag                                          24

<210> SEQ ID NO 4
<211> LENGTH: 22
<212> TYPE: DNA
<213> ORGANISM: Artificial
<220> FEATURE:
<223> OTHER INFORMATION: Synthetic

<400> SEQUENCE: 4
ggatcctgtc tcaaaatctc tg                                            22

<210> SEQ ID NO 5
<211> LENGTH: 51
<212> TYPE: DNA
<213> ORGANISM: Artificial
<220> FEATURE:
<223> OTHER INFORMATION: Synthetic

<400> SEQUENCE: 5
cgttttcgca tttatcgtga aacgctttcg cgttttttcgt gcgccgcttc a           51

<210> SEQ ID NO 6
<211> LENGTH: 56
<212> TYPE: DNA
<213> ORGANISM: Artificial
<220> FEATURE:
<223> OTHER INFORMATION: Synthetic

<400> SEQUENCE: 6
agatctgaag cggcgcacga aaaacgcgaa agtgtttcac gataaatgcg aaaacg       56

<210> SEQ ID NO 7
<211> LENGTH: 24
<212> TYPE: DNA
<213> ORGANISM: Artificial
<220> FEATURE:
<223> OTHER INFORMATION: Synthetic

<400> SEQUENCE: 7
tcgcgttttt agttcaccgc ttca                                          24

<210> SEQ ID NO 8
<211> LENGTH: 95
<212> TYPE: DNA
<213> ORGANISM: Artificial
<220> FEATURE:
<223> OTHER INFORMATION: Synthetic

<400> SEQUENCE: 8
attaatacga ctcactatag gggaattgtg agcggataac aattcccctc taggacctgc   60
aggcaaggag atatagagat gtgtataaga gacag                              95

<210> SEQ ID NO 9
<211> LENGTH: 21
<212> TYPE: DNA
<213> ORGANISM: Bacteriophage T7

<400> SEQUENCE: 9
attaatacga ctcactatag g                                             21
```

```
<210> SEQ ID NO 10
<211> LENGTH: 25
<212> TYPE: DNA
<213> ORGANISM: Artificial
<220> FEATURE:
<223> OTHER INFORMATION: Synthetic

<400> SEQUENCE: 10
ggaattgtga gcggataaca attcc                                          25

<210> SEQ ID NO 11
<211> LENGTH: 6
<212> TYPE: DNA
<213> ORGANISM: Artificial
<220> FEATURE:
<223> OTHER INFORMATION: Synthetic

<400> SEQUENCE: 11 aaggag                                                                6

<210> SEQ ID NO 12
<211> LENGTH: 19
<212> TYPE: DNA
<213> ORGANISM: Artificial
<220> FEATURE:
<223> OTHER INFORMATION: Synthetic

<400> SEQUENCE: 12
agatgtgtat aagagacag                                                 19
```

METHODS FOR OBTAINING DIRECTIONALLY TRUNCATED POLYPEPTIDES

CROSS-REFERENCE TO RELATED APPLICATION

This application claims priority to U.S. Provisional Patent Application Nos. 60/521,313, filed Mar. 30, 2004, and 60/572,446; filed May 19, 2004, each of which is specifically incorporated herein by reference in its entirety.

BACKGROUND OF THE INVENTION

I. Field of the Invention

The present invention relates generally to methods, compositions and kits for making unidirectionally or bidirectionally truncated polypeptides. The invention has broad applicability for research, industrial, and therapeutic uses, such as, but not limited to uses for engineering of proteins, including enzymes, identification of protein domains, changing protein functionality, epitope mapping, and for preparation of antigenic peptides for production of vaccines.

II. Description of Related Art

The introduction of deletions in nucleic acid sequences is a widely used method in molecular biology to study polypeptides encoded by the nucleic acid sequences.

Multiple procedures have been developed to generate deletions in nucleic acids, including procedures disclosed by Dunn et al. (U.S. Pat. No. 5,928,908; U.S. Pat. No. 5,968,768; and U.S. Pat. No. 6,248,569); Shen et al. (U.S. Pat. No. 5,356,773); Yohda et al. (DNA Research, 2: 175-181, 1995); Zhu and Marshall (BioTechniques, 18: 222-224, 1995); and Henikoff et al. (Gene, 28: 351-359, 1984 and U.S. Pat. No. 4,843,003). Other procedures for generating deletions have utilized variations of PCR (e.g., Pues et al., Nucleic Acids Res. 25: 1303-1304, 1997). All of the above are incorporated herein by reference in their entireties.

The current techniques for generating deletions in a target sequence are time-consuming and wasteful and what is needed are procedures to make deletions of nucleic acids that encode proteins that are less time-consuming and more efficient. What is further needed are procedures that allow the generation of deletions without the need to first clone the nucleic acid sequence of interest into a vector. Also, what is needed are methods to make large quantities of deletions in a random fashion, so that surprising and unexpected results can be obtained.

DNA transposons are mobile elements that can move from one position in a genome to another. In nature, transposons play roles in evolution as a result of their movements within and between genomes. Transposons are relatively simple genetic systems, consisting of some genetic sequence bounded by inverted terminal repeats and a transposase enzyme that acts to cut the transposon out of one source of DNA and paste it into another DNA sequence. Autonomous transposons carry the transposase gene inside the transposon whereas non-autonomous transposons require another source of transposase for their mobilization.

Multiple studies of transposition have been have been published (Devine et al., U.S. Pat. No. 5,677,170; Devine et al., U.S. Pat. Nos. 5,728,551 and 5,968,785; Hackett et al., International Patent Application No. WO 98/40510; Plasternak et al., International Patent Application No. WO 97/29202; Reznikoff et al., International Patent Application No. WO 98/10077; Craig, International Patent Application No. WO 98/37205; Strathman et al., Proc. Nat. Acad. Sci. USA 88: 1247-1250, 1991; Phadnis et al., Proc. Nat. Acad. Sci. USA 86: 5908-5912, 1989; Way et al., Gene 32: 269-279, 1984; Kleckner et al., Method. Enzymol. 204: 139-180, 1991; Lee et al., Proc. Nat. Acad. Sci. USA 84: 7876, 1987; Brown et al., Cell, 49: 347-356, 1987; Eichinger et al., Cell, 54: 955-966, 1988; Eichinger et al., Genes Dev., 4: 324-330, 1990; all of which are incorporated herein by reference in their entireties.

A number of studies have reported on deletions generated by transposons or the use of transposons to generate deletions for using in nucleic acid sequencing. Among these are articles by Ahmed (J. Mol. Biol., 178: 941-948, 1984); Hattori et al. (Nucleic Acids Res. 25: 1802-1808, 1997); Jilk et al. (J. Bacteriology, 175: 1264-1271, 1993); Krishnan et al. (Nucleic Acids Res. 23: 117-122, 1995); Morita et al., (DNA Research, 3: 431-433, 1996); Sugino et al. (U.S. Pat. No. 6,265,159 BI); Wang et al. (J. Bacteriology, 176: 6348-6354, 1990); and Wang et al. (Proc. Natl. Acad. Sci., 90: 7874-7878, 1993), all of which are incorporated herein by reference in their entireties.

Methods for using vectors with specially positioned and oriented transposon end sequences and a transposase were used for making unidirectional deletions in a target sequence cloned into the vector for a variety of purposes, as described by York et al. (Nucleic Acids Res. 26: 1927, 1998 and U.S. Pat. No. 5,948,622). These researchers also described how the methods could be used for making unidirectionally truncated polypeptides.

In U.S. Pat. No. 6,593,113, which is incorporated herein by reference in its entirety, Tenkanen et al. describe the use of a transposition reaction and a subsequent amplification reaction for providing templates for DNA sequencing. The inventors do not envision a method for making truncated polypeptides.

WO03/87370, incorporated herein by reference in its entirety, teaches a method for producing deletion derivatives of polypeptides by inserting transposons that contain translation stop signals into target nucleic acid sequences that have been cloned into vectors. The need to first clone a nucleic acid sequence of interest is time consuming and lacks efficiency.

BRIEF SUMMARY OF THE INVENTION

The present invention provides, in part, novel methods, compositions and kits for obtaining random directionally truncated polypeptides encoded by a target sequence. Embodiments of the invention enable obtaining randomly truncated polypeptides that are unidirectionally truncated from either the amino-terminal end or from the carboxyl-terminal end. Still other embodiments enable obtaining polypeptides that are bidirectionally truncated from both amino- and carboxyl-terminal ends. Additional aspects of the invention will be understood from the specification below.

In some embodiments, the methods, compositions, and kits of the present invention provide a method for obtaining a truncated polypeptide, the method comprising: (a) inserting a transposon into a target sequence to generate a transposon-containing target sequence; (b) amplifying the transposon-containing target sequence to generate an amplification product comprising sequence from the transposon and a truncated (e.g., unidirectionally or bidirectionally truncated) portion of said target nucleic acid; and (c) transforming said amplification product into a host cell (e.g., by ligating said amplification product to generate a circular amplification product). In some embodiments, the method further comprises the steps of d) selecting host cells that contain the amplification product; and e) obtaining a truncated protein generated by said host cells.

In some preferred embodiments the methods comprise the following steps:

(a) contacting a target nucleic acid with a transposon under conditions whereby insertion of the transposon into the target nucleic acid occurs, wherein the transposon encodes a selectable marker that is expressible in a host cell and an origin of replication that is capable of directing replication in the host cell;

(b) amplifying the target nucleic acid into which the transposon has inserted to obtain an amplification product that is delimited by a first primer that anneals (e.g., selectively anneals) to one strand of the target nucleic acid and a second primer that anneals (e.g., selectively anneals) to the transposon in an opposite polarity to the first primer, the amplification product comprising nucleic acid sequences from the transposon and from a unidirectionally-truncated target nucleic acid;

(c) ligating the amplification product to obtain a circular amplification product;

(d) transforming the circular amplification product into a host cell, wherein the circular amplification product is replicated using the origin of replication from the transposon and the selectable marker encoded by the transposon is expressed;

(e) selecting host cells that contain the selectable marker encoded by nucleic acid sequences from the transposon that comprise the circular amplification product;

(f) obtaining an RNA transcript by transcription of the unidirectionally-truncated target nucleic acid encoded by the circular amplification product;

(g) obtaining a unidirectionally-truncated polypeptide encoded by translation of an RNA transcript obtained by transcription of the unidirectionally-truncated target nucleic acid encoded by the circular amplification product; and (h) purifying the unidirectionally-truncated polypeptide.

The insertion of a transposon into a "target nucleic acid" or a "target nucleic acid sequence" or a "target sequence" or a "target DNA" can be carried out in vitro or in vivo in a cell.

In preferred embodiments, the transposon for the insertion reaction comprises a gene that encodes a selectable marker, such as an antibiotic resistance gene, that is expressible in and confers resistance to the host cell and an origin of replication (ori) from any source that enables replication of a circular double-stranded DNA that comprises the ori in the host cell. Preferably, the selectable marker encodes a single gene that encodes resistance to a chemical substance.

In addition, the transposon can comprise a promoter sequence for an RNA polymerase that recognizes and is capable of directing in vitro or in vivo transcription of a DNA sequence that is functionally joined to the promoter. If present in the transposon, the promoter is oriented so as to direct transcription outward towards one of the two transposon recognition sequences at the ends of the transposon. If a promoter is present in the transposon, the transposon can also comprise additional sequences for translation downstream of the promoter sequence, such as but not limited to a ribosome binding site and a translation start codon (also referred to as a "translation start signal").

Following insertion of the transposon into the target sequence, preferred methods of the present invention comprise an amplification reaction, preferably a PCR amplification reaction, using a first primer that anneals selectively to one strand of the target nucleic acid at a fixed point and a second primer that anneals selectively to the transposon in an opposite polarity to the first primer. In addition to comprising at least a portion of the target sequence, which is delimited by the primer that anneals to the target sequence, an amplification product obtained preferably also comprises sequences that encode the selectable marker and an origin of replication (e.g., ori). In some embodiments in which a carboxyl-truncated polypeptide is obtained and in which embodiments the transposon comprises a promoter sequence for transcription and other sequences, such as a ribosome binding site (RBS) and a start codon for translation, the second primer preferably primes a sequence that is interior to the transposon end sequence and its 5'-end encodes the translation start codon so that nucleotides that encode the transposon end sequence are translated into amino acids and polypeptides. Thus, carboxyl-truncations of the target sequence do not have the additional amino acids encoded by the transposon end sequences.

In preferred embodiments of aspects of the invention in which carboxyl-truncated polypeptides are obtained, translation stop codons for all three reading frames are present either within the transposon end sequences or near to the left transposon end so that translation is terminated at or near to the end of the amino-terminus of the carboxyl-truncated polypeptides obtained.

In embodiments in which the transposon does not comprise a promoter sequence for transcription or other sequences for translation, a primer referred to as a "promoter primer," is preferably used. The promoter primer has a "5'-flap" or "5'-tail" that does not anneal to the transposon and that encodes a promoter sequence, a ribosome binding site (RBS) and a start codon for translation so that the resulting amplification product comprises these sequences. In these embodiments, the translation start codon is preferably at the 5'-end of the promoter primer so that it can subsequently be joined directly to a 3'-end of a target sequence without adding any extra nucleotides from the transposon end sequences that could be translated into extra amino acids at the carboxyl-end of polypeptides having carboxyl-truncations of the target sequence.

In still other embodiments a promoter, a ribosome binding site and a translation start codon are present in the target sequence and are amplified therefrom.

Since transposition generally occurs at random sites into the target sequence, different amplification products will vary in length, depending on where the transposon inserted, but the ends of the amplification products comprising a portion of the target sequence that was primed by the first primer will all be the same (unless desired otherwise through use of multiple amplification primers, degenerate primers, non-specific primers, etc.). Thus, the amplification products can be viewed as a population of unidirectionally truncated molecules of the target sequence.

The linear unidirectionally truncated amplification products are then ligated to obtain circular amplification products comprising double-stranded DNA having a selectable marker and an ori. Following transformation into a suitable host cell, such as but not limited to a competent *E. coli* host cell, the ori and selectable marker enable host cells containing circular amplification products to be replicated and selected on medium containing a chemical substance for which resistance is encoded by the marker. This process can be thought of as similar to molecular cloning.

In some embodiments of the invention in which the host cell has an expressible RNA polymerase gene for an RNA polymerase that recognizes the promoter in the circular amplification product and suitable translation proteins and factors for translation of the resulting transcription product, unidirectionally-truncated polypeptides can be obtained in vivo. In other embodiments, transcription and/or translation are carried out in vitro using cell-free systems known in the art. In preferred embodiments, the promoter that directs transcription is a T7-type RNA polymerase promoter and the RNA polymerase is a T7-type RNA polymerase that recognizes the promoter. Most preferably, the RNA polymerase and promoter are chosen from among T7 RNAP, T3 RNAP and SP6 RNAP and the corresponding cognate promoters.

The invention also comprises methods, compositions and kits for obtaining a bidirectionally truncated polypeptide, the method comprising, for example, using a construct generated above that produces unidirectionally truncated polypeptides and further altering the construct so as to produce bidirectional polypeptides by repeating the process. A preferred method for doing so is as follow:

(a) obtaining a first circular amplification product comprising a unidirectionally-truncated target nucleic acid that encodes a unidirectionally-truncated polypeptide using a first transposon as described above;

(b) contacting the first circular amplification product with a second transposon that encodes a second selectable marker under conditions wherein a transposase binds to the second transposon and catalyzes insertion of the second transposon into the target nucleic acid sequences of the first circular amplification product;

(c) obtaining a second amplification product by amplification of the first circular amplification product into which the second transposon has inserted using a forward primer that anneals (e.g., selectively) to one strand of the first circular amplification product and a reverse primer that anneals selectively to the second transposon in an opposite polarity to the forward primer, wherein the second amplification product comprises nucleic acid sequences of the first transposon at one end of the bidirectionally-truncated target nucleic acid sequence and nucleic acid sequences of the second transposon at the opposite end of the bidirectionally-truncated target nucleic acid sequence;

(d) ligating the second amplification product to obtain a second circular amplification product;

(e) transforming the second circular amplification product into a host cell, wherein the second circular amplification product is replicated and the selectable markers encoded by the first transposon and the second transposon are expressed;

(f) selecting host cells that contain the selectable marker encoded by nucleic acid sequences from the first and second transposons that are in the second circular amplification product;

(g) obtaining an RNA transcript by transcription of the bidirectionally-truncated target nucleic acid encoded by the second circular amplification product;

(h) obtaining a bidirectionally-truncated polypeptide encoded by translation of the RNA transcript from the bidirectionally-truncated target nucleic acid encoded by the second circular amplification product; and (i) purifying the bidirectionally-truncated polypeptide.

In this embodiment for obtaining bidirectionally truncated polypeptides, the transposase used to catalyze transposition of the first and the second transposons can be the same or different. If the same transposase is used for transposition of both the first and second transposons, preferably the transposase is a wild-type, or a mutant or derivative of MuA transposase.

In other embodiments for obtaining a bidirectionally truncated polypeptide a first and a second transposon are used simultaneously to obtain a bidirectionally truncated polypeptide, i.e. a target nucleic acid is contacted with two different transposons under conditions whereby simultaneous insertion of both transposons into the target nucleic acids occurs, wherein the first transposon encodes a first selectable marker that is expressible in a host cell and an origin of replication that is capable of directing replication in the host cell and wherein the second transposon encodes a second selectable marker.

Still other embodiments of the invention for obtaining a bidirectionally truncated polypeptide comprise methods, compositions and kits wherein only transposon end sequences are used in place of a second transposon. The second linear amplification products are amplified using a forward primer that anneals to the first truncated end of the truncated target sequence and a reverse primer that anneals to the transposon end sequence. Then the second linear amplification product is circularized by ligation. In this embodiment, replication and selection of host cells transformed by the second circular amplification occurs using the ori and the selectable marker encoded by the first transposon. It is preferable that different transposases are used for the transposition of the first transposon and the second transposition with transposon end sequences because many transposase enzymes can recognize and cleave transposon end sequences remaining from a first transposition. However, if the same transposase is used, preferably the transposase is a wild-type, mutant or derivative of MuA transposase because this enzyme requires perfect cleaved R1 and R2 transposon end sequences in order to catalyze transposition, and MuA transposase does not cleave internal R1 and R2 ends that are inserted into another sequence.

The invention also comprises compositions and kits for obtaining unidirectionally or bidirectionally truncated polypeptides including any set or subset of reagents useful for carrying out the methods as well as any other desired components that may be used in a research, diagnostic, or therapeutic context (e.g., buffers, controls, instructions, software, etc.).

BRIEF DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

RNA polymerase promoter (SEQ ID NO:9), a lac operator (SEQ ID NO:10), and a ribosome binding site (SEQ ID NO:11), a kanamycin resistance gene, and an R6Kγ origin of replication.

Figure 1A:
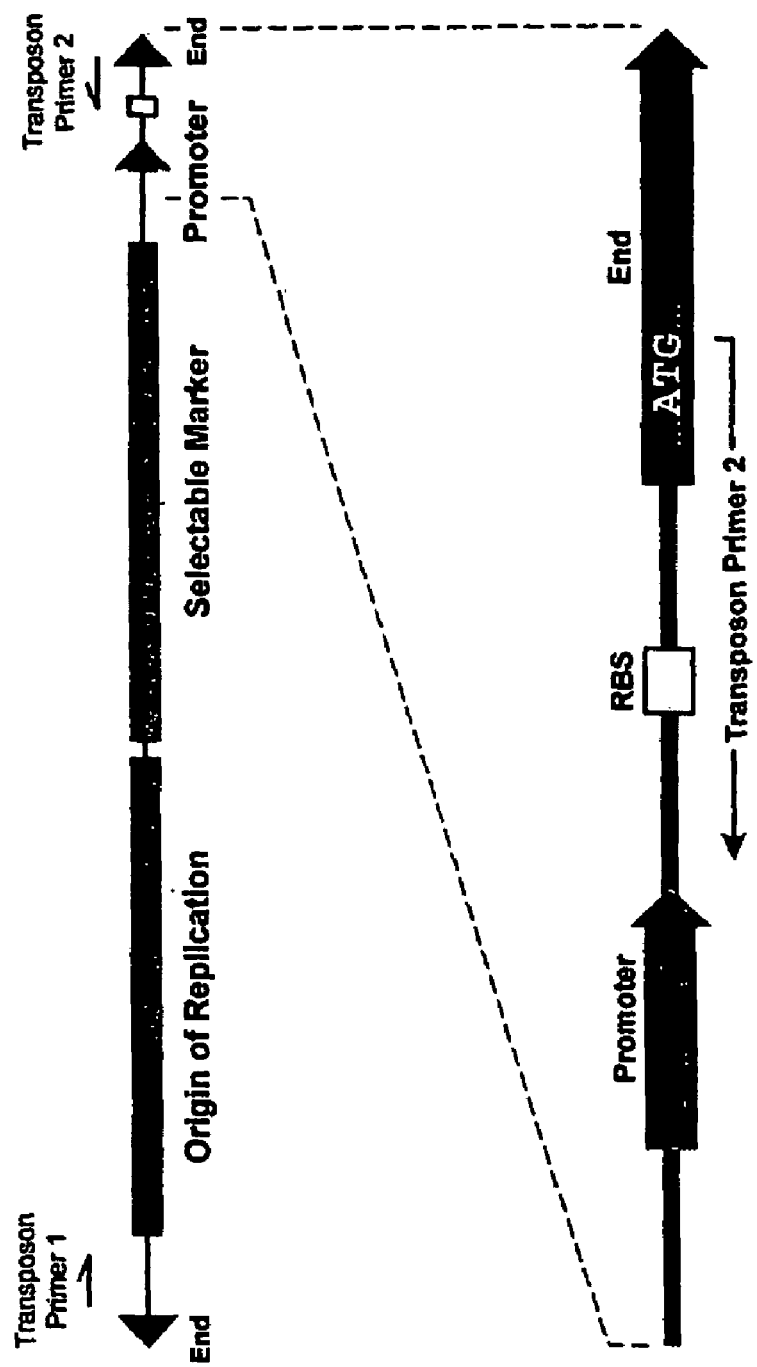
FIG. 1A shows a transposon that can be used for the present invention to make insertions into a target sequence. The transposon comprises a selectable marker that is expressible in a host cell, an origin of replication that is expressible in the host cell, an RNA polymerase promoter, a ribosome binding site, and a translation start signal. Also shown are the ends of the transposon as inverted repeats, as well as one primer set and their annealing sites which can be used to make target sequences that are unidirectionally truncated from each end.
Figure 1B:
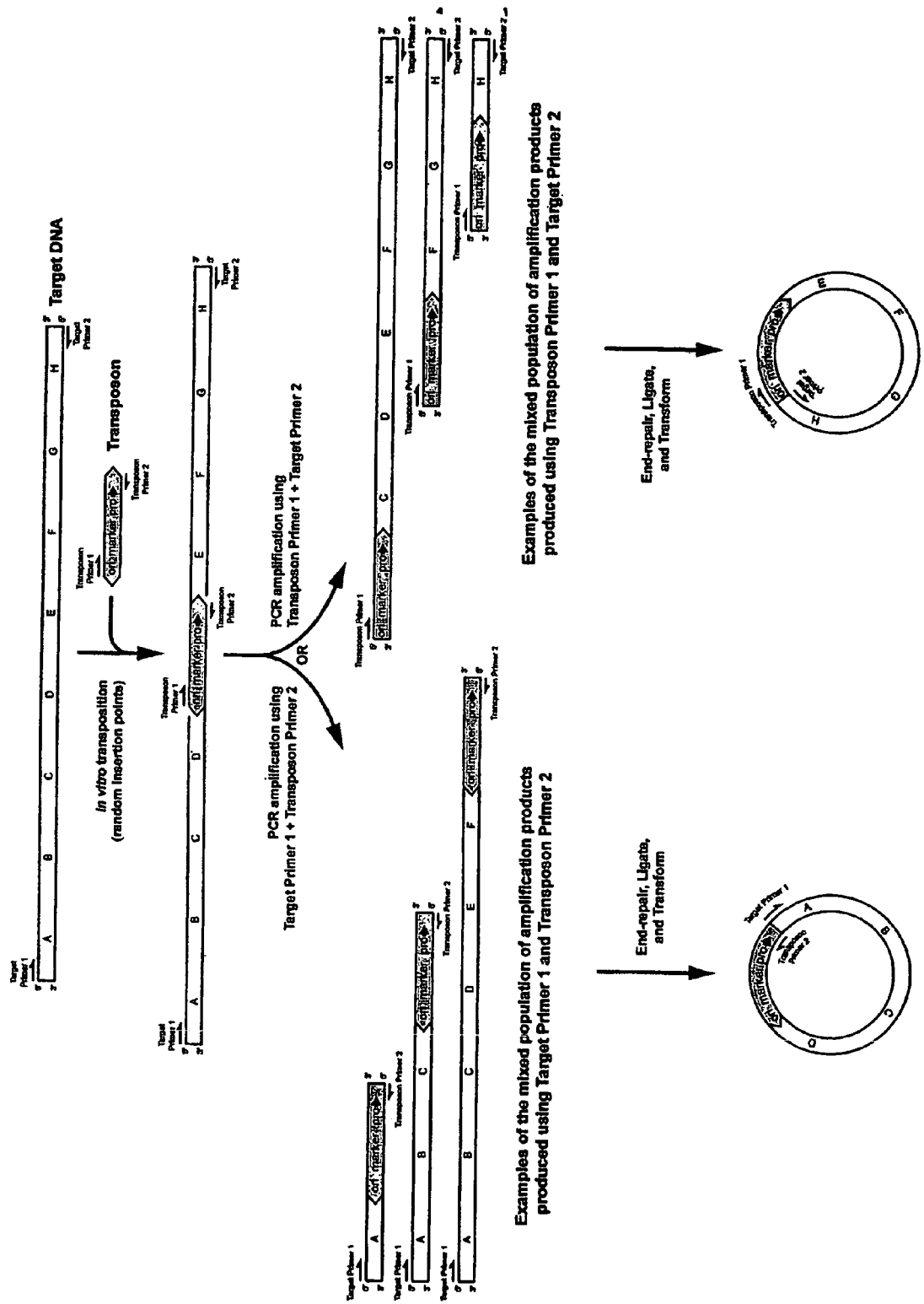
FIG. 1B illustrates several steps of an embodiment of the present invention: a step for insertion of a transposon into a target DNA, a subsequent amplification step with two different sets of primers resulting in two different types of amplification products with multiple different random insertion points, and a ligation step resulting in circular amplification products that can each be transcribed to obtain a transcript, which in turn can be translated to obtain a unidirectionally truncated polypeptide.
Figure 2A:
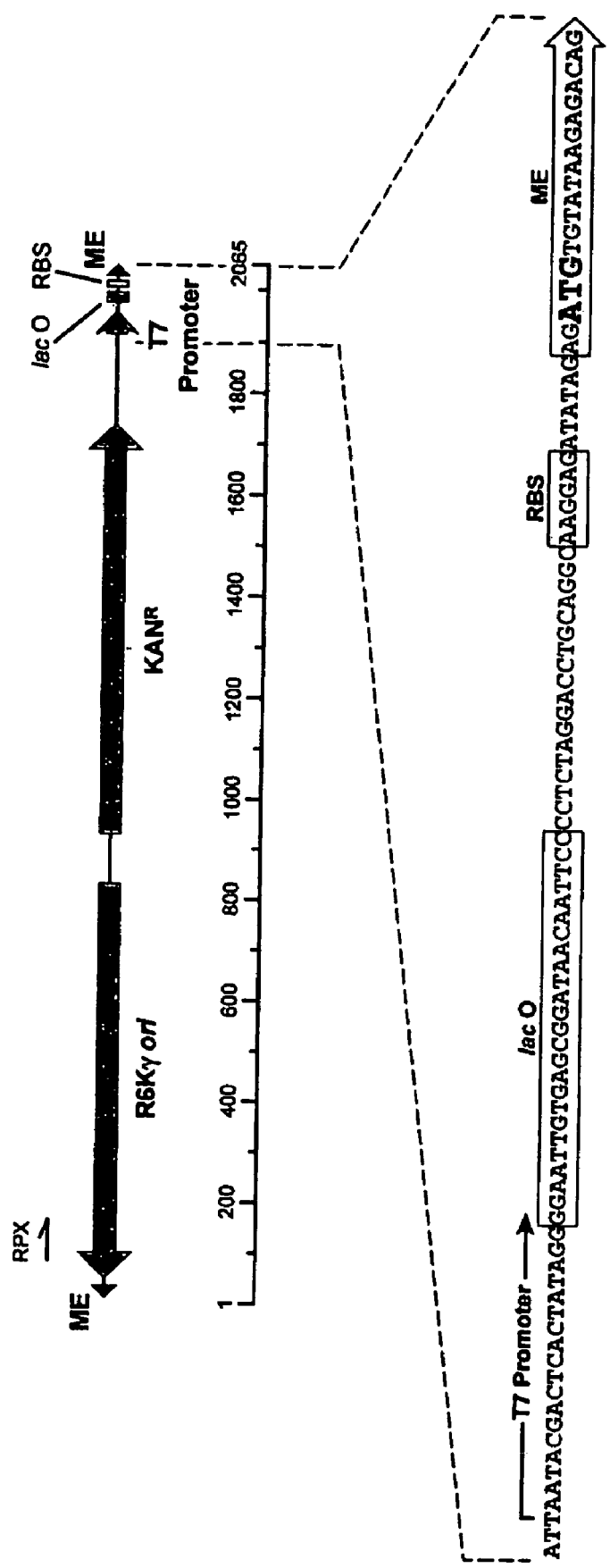
FIG. 2A (SEQ ID NO:8) shows an EZ::TN™<R6Kγori/KAN-2/T7Exp> Transposon which can be used in the present invention. The terms "EZ::TN™" and "EZ-Tn5™" are used interchangeably herein. The transposon comprises two mosaic ends of 19 base pairs each (SEQ ID NO:12), facing opposite directions, said mosaic ends having a translation start signal (ATG). In addition, the transposon comprises a T7
Figure 2B:
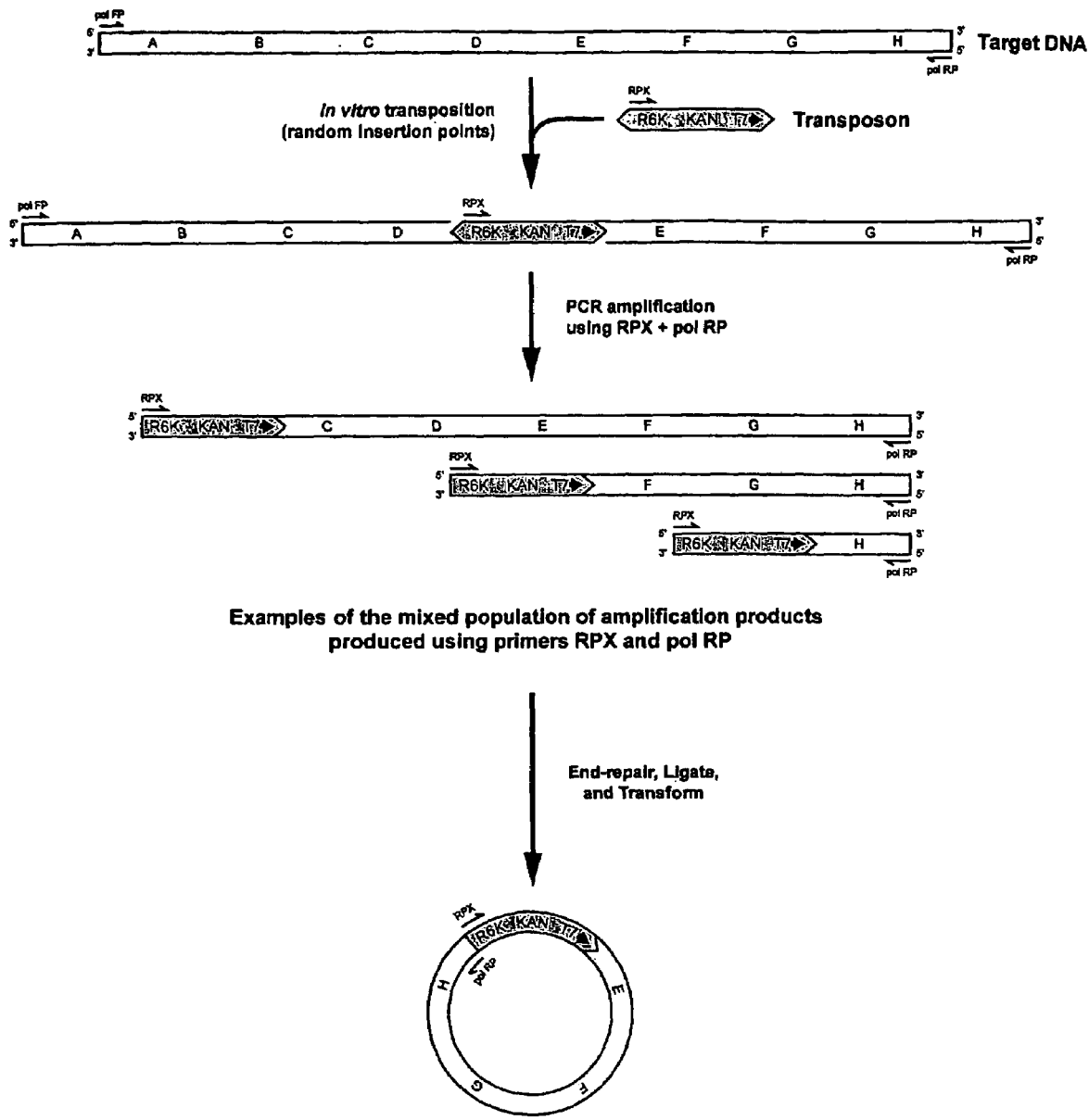

FIG. 2B illustrates one aspect of the present invention in which the transposon from FIG. 2A is inserted into a target sequence, followed by PCR amplification. Shown are the locations of primers used in the PCR amplification. Depending on the transposon insertion point, which is random, a multitude of PCR amplification products having different sizes is generated, all of which represent unidirectional deletions from the same end. Three unidirectionally truncated target sequences are shown. The figure further illustrates obtaining a circular amplification product after end-repair and self-ligation.

Figure 3:
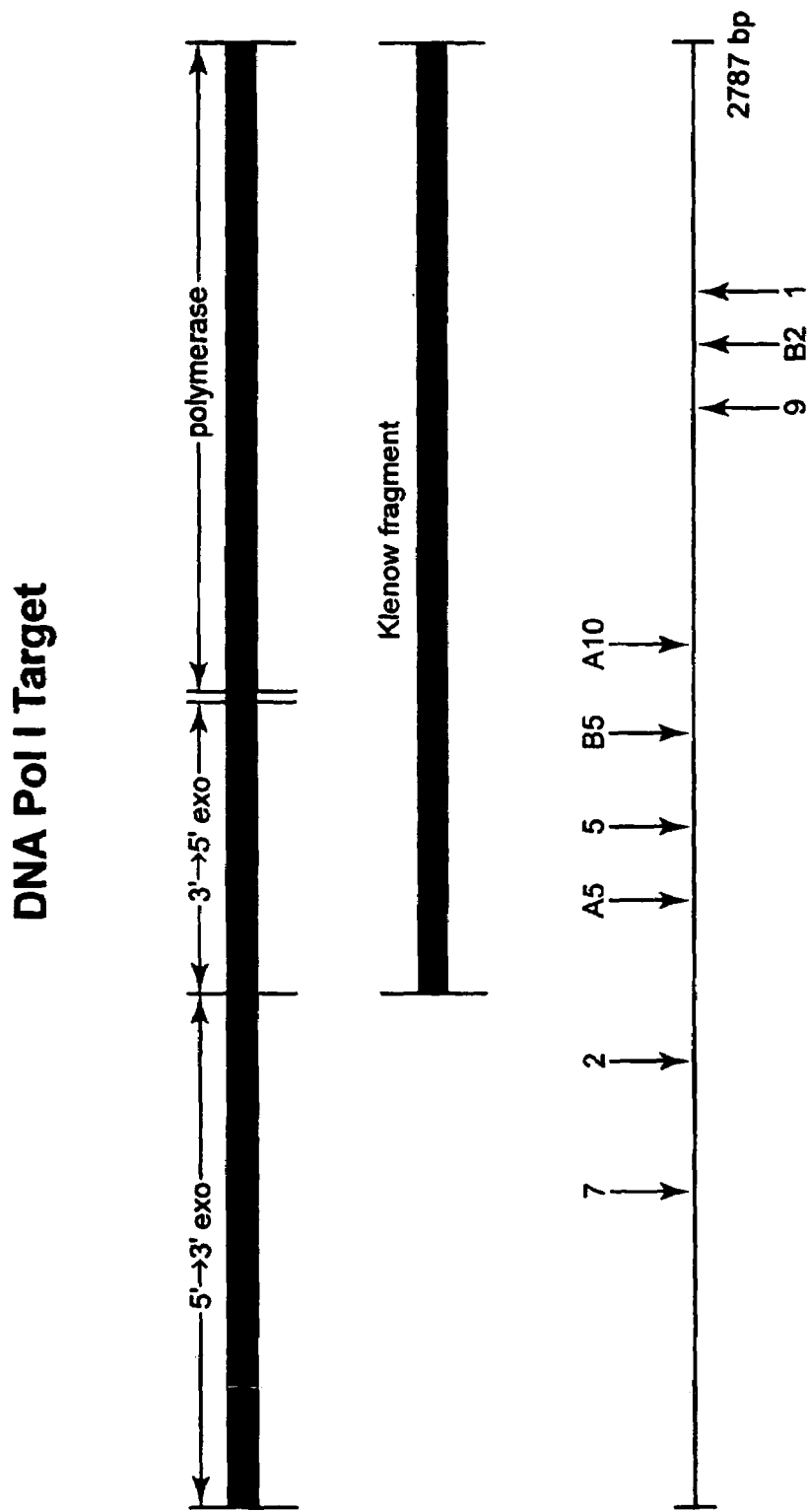

FIG. 3 illustrates E. coli DNA polymerase I target DNA with its three functional domains: a 5'-to-3' exonuclease domain, a 3'-to-5' exonuclease domain and a DNA polymerase domain. Also illustrated is a control DNA that encodes a Klenow fragment that lacks 5'-to-3' exonuclease activity. The bottom part of the figure shows examples of identified transposition sites into a target nucleic acid when a first transposon was used to obtain unidirectional truncations in EXAMPLE 3 (downward arrows) and when a second transposon was used to obtain bidirectional truncations in EXAMPLE 6 (upward arrows).

Figure 4:
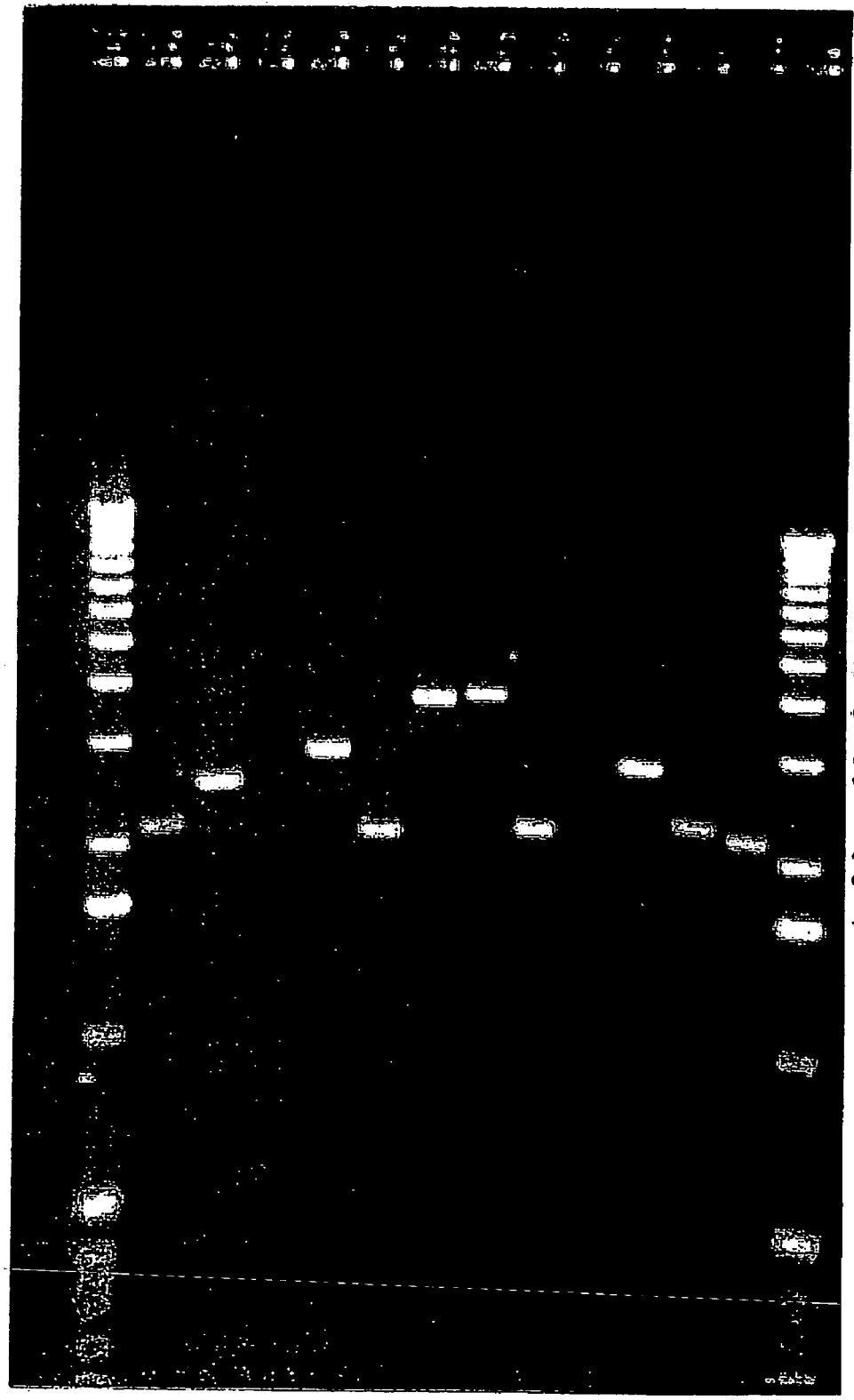

FIG. 4 shows results of PCR screening of 12 colonies obtained in EXAMPLE 3. The figure shows an agarose gel having size markers in lanes 1 and 14. The PCR products obtained from colonies range in size from about 2 kbp to about 4.8 kbp (lanes 2, 3, 5-9, 11-13), indicating that the respective clones comprise unidirectionally truncated target nucleic acids. Lanes 4 and 10 are empty, which indicates that colony PCR did not result in any PCR products.

Figure 5:
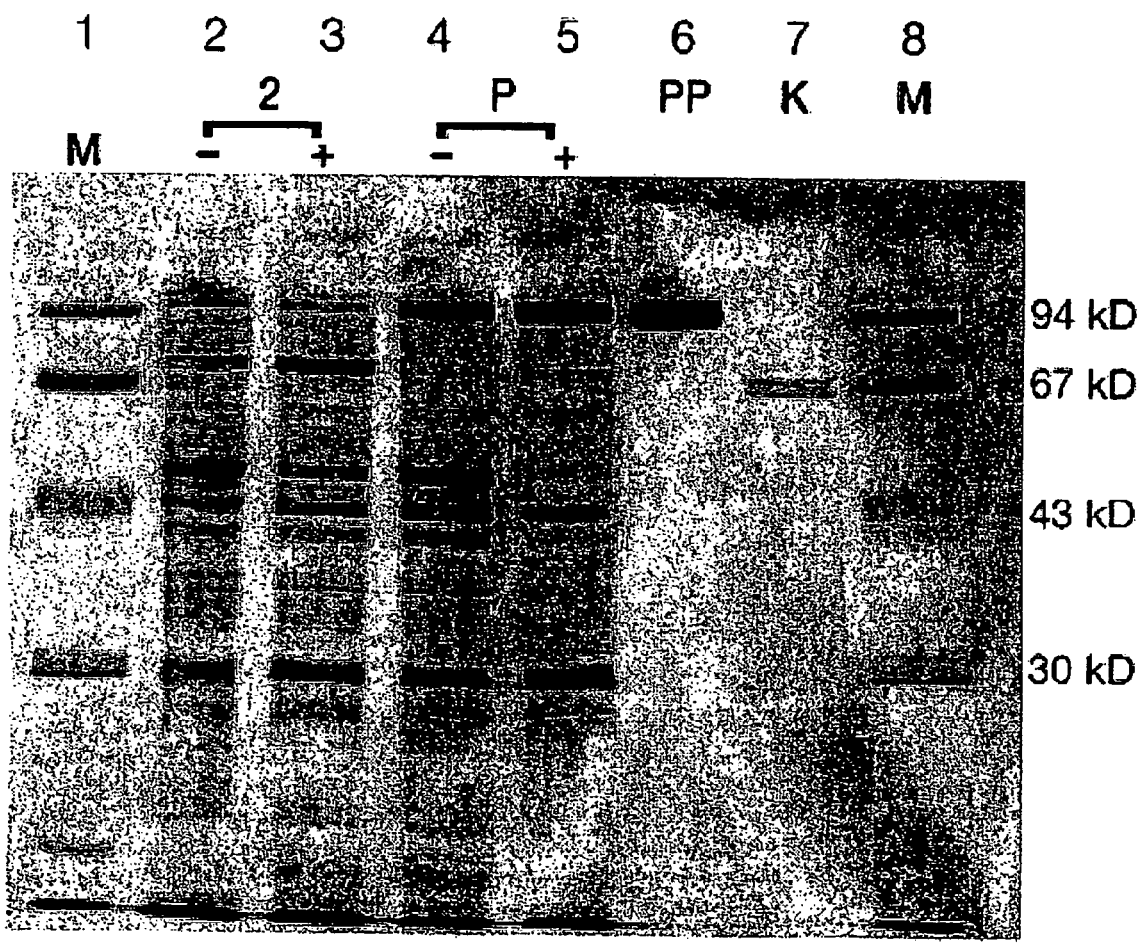

FIG. 5 shows an SDS-polyacrylamide gel of polypeptides obtained in EXAMPLE 5. Lanes 1 and 8 are protein size markers ranging in size from 30 kD to 94 kD. Lanes 6 and lane 7 contain purified untruncated E. coli DNA polymerase I and purified Klenow fragment, respectively, as controls. Lane 2 shows the protein bands of the uninduced E. coli DNA polymerase I truncation clone 2, and lane 3 shows the protein bands obtained from the same clone after protein expression was induced with IPTG as described in EXAMPLE 5. Lanes 4 and 5 show a control for expression of a clone of full-length untruncated E. coli DNA polymerase I, before and after IPTG induction, respectively.

The polymerase truncation clone in lane 3 shows an inducible band at a size that is slightly larger than the size of the Klenow fragment (lane 7). This was expected, since the nucleic acid encoding the truncated E. coli DNA polymerase I in clone 2 is slightly larger than the sequence that encodes the Klenow fragment, as shown with a downward arrow in FIG. 3. Therefore, the figure shows that a truncated polypeptide corresponding in size to the truncated nucleic target nucleic acid was obtained.

Figure 6:
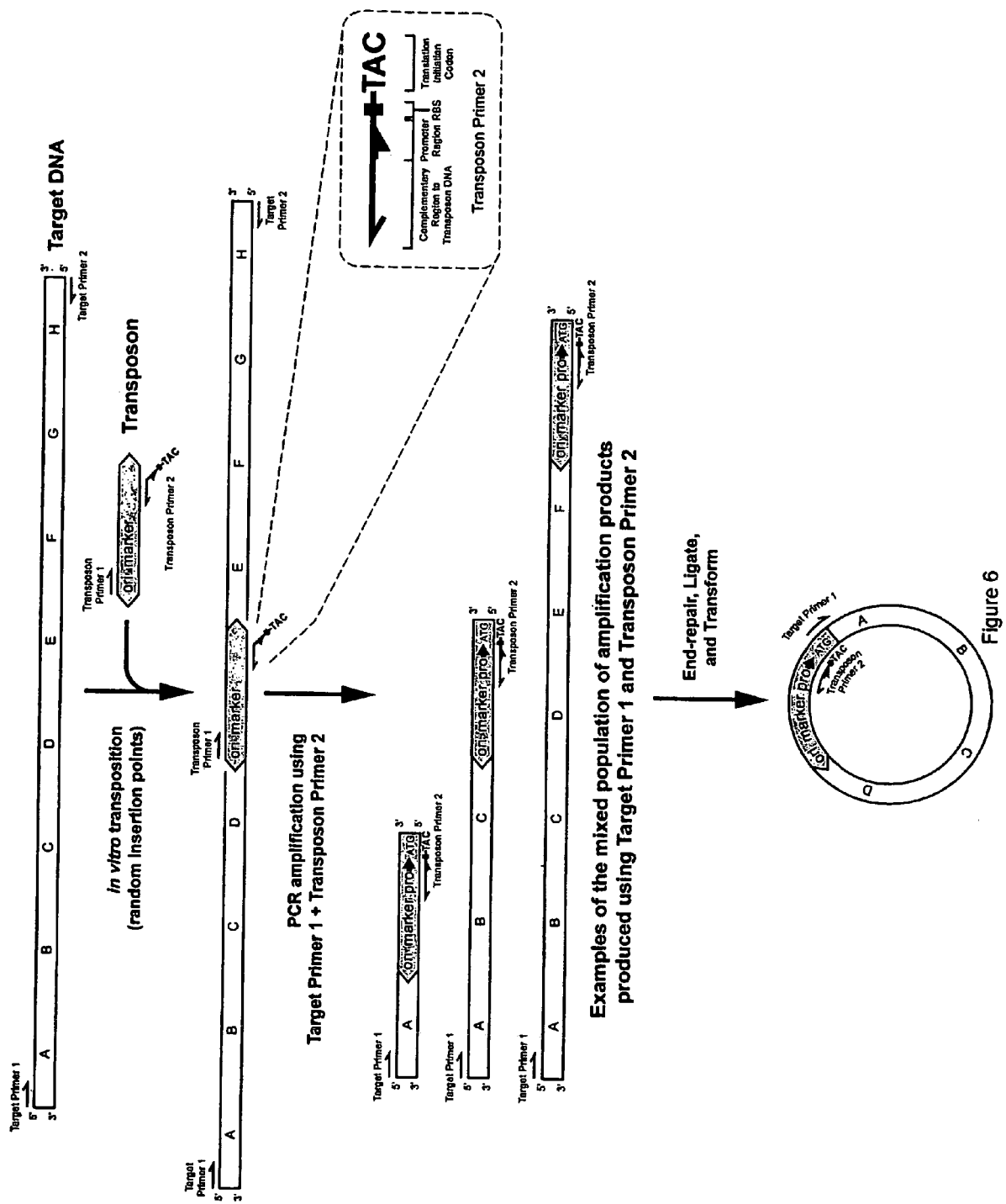

FIG. 6 exemplifies a method for generating carboxyl-terminal truncations of a polypeptide. Following random insertion of a transposon into a target sequence in vitro or in vivo, PCR amplification is performed using a first amplification primer that anneals to and amplifies the target sequence encoding the amino-terminal end of the polypeptide and a second amplification primer that has a 3'-portion that anneals to a site in the inserted transposon that is internal with respect to the transposon end sequence, and wherein the second amplification primer also comprises a 5'-portion comprising a tail that encodes a promoter sequence, a ribosome binding site and an ATG translation start codon. The second amplification primer is also sometimes referred to as a "promoter primer" herein.

Following the amplification, the PCR products are end-repaired and ligated, which results in the promoter sequence being functionally joined to the target sequence so that transcription from the promoter and translation, either in vitro or in vivo, yields polypeptides having carboxyl-terminal truncations of the polypeptide encoded by the target sequence. One aspect of this embodiment of the invention is that, since the second amplification primer anneals to the transposon inside of the transposon end sequence, the PCR amplification product does not encode additional amino acids that would otherwise have been added to the amino-terminus of the resulting polypeptide if the transposon end sequence had been present.

In preferred embodiments of this aspect of the invention, translation stop codons for all three reading frames are present either within the transposon end sequences or near to the left transposon end so that translation is terminated at or near to the end of the amino-terminus of the carboxyl-truncated polypeptides obtained.

In general, the use of a promoter primer is only useful for amplification of truncated target sequences that encode carboxyl-terminal truncations of the polypeptide, as described above and as shown in FIG. 6. This is because the promoter cannot be joined directly to the target sequence if a promoter primer is used to obtain an amplification product of a target sequence encoding an amino-terminal truncation. Therefore, embodiments of the invention that use a transposon having a promoter for transcription and a ribosome binding site and an ATG translation start codon for translation within the amplified transposon sequence and close to the appropriate transposon end sequence are preferred for obtaining polypeptides that have amino-terminal truncations of the polypeptide encoded by the complete target sequence.

DETAILED DESCRIPTION OF THE INVENTION

The present invention relates to novel methods, compositions, and kits for obtaining directionally-truncated polypeptides.

Some embodiments of the present invention are related to obtaining "unidirectionally truncated polypeptides." By "unidirectionally truncated" is meant that the "truncations" or missing amino acids are from only one of the ends of the polypeptide encoded by a target nucleic acid sequence of interest; i.e., one end of the polypeptide is "fixed" or "anchored," meaning that it comprises all of the amino acids encoded by either the 5'-end or the 3'-end of the target nucleic acid sequence and is constant, while the other "truncated" or "deleted" end varies and lacks some of the amino acids encoded by the target nucleic acid sequence that is treated using a method of the invention. Thus, the length of the polypeptide from the fixed or anchored end also varies.

Other embodiments of the present invention are related to obtaining "bidirectionally truncated polypeptides." By "bidirectionally truncated" is meant that the "truncations" or missing amino acids are from both ends of the polypeptide encoded by a target nucleic acid sequence of interest; i.e., the bidirectionally truncated polypeptide lacks some of the amino acids encoded by both the 5'-end and the 3'-end of the target nucleic acid sequence that is treated using a method of the invention. In general, a bidirectionally truncated polypeptide is obtained by first obtaining a unidirectionally truncated or deleted target nucleic acid sequence and then using this unidirectionally truncated target nucleic acid sequence as a new target nucleic acid for obtaining unidirectional truncations from the other previously-untruncated end; i.e., the truncated end of the first unidirectionally truncated or deleted target nucleic acid sequence becomes the fixed or anchored end in a process or method for obtaining additional truncations.

Both unidirectionally truncated polypeptides and bidirectionally truncated polypeptides are referred to herein as "directionally truncated" since the truncations in both cases are from the ends of the polypeptide encoded by the target nucleic acid sequence rather than from an internal portion of the polypeptide encoded by a target nucleic acid sequence. Nucleic acid sequences that encode the respective unidirectionally truncated or bidirectionally truncated or directionally truncated polypeptides may be referred to as "unidirectionally truncated" or bidirectionally truncated" or "directionally truncated" (or sometimes as "directionally deleted") target nucleic acids or target nucleic acid sequences or target sequences.

A. Methods of the Invention

A first step in an embodiment of the invention for obtaining unidirectionally truncated polypeptides comprises contacting a target nucleic acid with a transposon under conditions whereby insertion of the transposon into the target nucleic acid occurs, wherein the transposon encodes a selectable marker that is expressible in a host cell and an origin of replication that is capable of directing replication in the host cell.

A "target DNA" or a "target nucleic acid" is a DNA of interest. A target nucleic acid can be double-stranded DNA (dsDNA) from any source in purified or unpurified form, whether present in vitro or in vivo in a cell. For example, a target nucleic acid can be dsDNA as mitochondrial DNA, chloroplast DNA, chromosomes, plasmids or other episomes, the genomes of bacteria, yeasts, viruses, viroids, mycoplasma, molds, or other microorganisms, or genomes of fungi, plants, animals, or humans. Single-stranded DNA (ssDNA) can be converted to dsDNA in vitro for use as a target nucleic acid by methods known in the art, such as but not limited to primer extension. Also, RNA, such as mRNA, can be converted to ssDNA by any of the reverse transcription methods known in the art and then the ssDNA can be converted to dsDNA for use as a target nucleic acid of the invention. The term "target nucleic acid sequence" or "target sequence" refers to the particular nucleotide sequence of the target nucleic acid that is treated using methods of the invention to obtain a truncated polynucleotide. A "target sequence" comprises a sequence within a target nucleic acid and is generally limited only by the size of the nucleic acid itself or by the size of the amplification product that can be obtained by amplification during a method of the invention. Current methods permit PCR amplification of sequences up to about 20 to 50 kilobase pairs, but the invention is intended to apply to a target sequence of any size that is amplifiable following insertion of a transposon as described herein. In some cases herein, the terms "target DNA," and "target nucleic acid," and "target nucleic acid sequence," and "target sequence" are used interchangeably to refer to the nucleic acid that is contacted with a transposon although not all of the sequence of the nucleic acid may be amplified during the respective method of the invention.

A "transposon" of the present invention is a segment of DNA that can insert itself into a target DNA at random or at almost random locations in the presence of a cognate transposase that recognizes and binds to the "transposon end sequences" or "transposon recognition sequences" or simply the "end sequences" to form a "complex" or a "synaptic complex" or a "Transposome™ complex" (trademark of EPICENTRE Technologies, Madison, Wis.). The transposons used for the present invention can contain only the necessary DNA capable of forming a functional complex with a transposase or integrase enzyme and possibly with other enzymes needed in a transposition reaction. The term "transposon" is intended to mean a DNA segment or segments which is/are recognizable by a transposase or an integrase enzyme and which is/are capable of forming a functional complex for a transposition reaction. The transposons used for some embodiments of the present invention, which are preferred embodiments, contain an origin of replication ("ori"), a sequence encoding a selectable marker and at least one binding site for a primer. In some embodiments for obtaining bidirectionally-truncated polypeptides, truncation of the other end of a polypeptide that already comprises a unidirectionally truncated polypeptide can be obtained using only the transposon end sequences rather than using a transposon with two transposon end sequences.

The term "transposase" with respect to the present invention is intended to mean an enzyme capable of forming a functional complex with a transposon or transposon end sequences needed in a transposition reaction. A transposase of the invention also includes integrases from retrotransposons and retroviruses.

A "transposition reaction" is a reaction wherein a transposon or transposon end sequences are inserted into a target DNA at random sites or almost random sites. Components in a transposition reaction typically comprise a transposase and a transposon or transposon end sequences, as well as other components needed to form a functional transposition complex. The method of this invention is exemplified by employing a transposition complex formed by a hyperactive Tn5 transposase and a Tn5-type transposon (Goryshin, I. and Reznikoff, W. S., J. Biol. Chem., 273: 7367, 1998) or by a MuA transposase and a Mu transposon comprising R1 and R2 end sequences (Mizuuchi, K., Cell, 35: 785, 1983; Savilahti, H, et al., EMBO J., 14: 4893, 1995). However, the particular transposon system used is not critical for the invention. Any transposition system that is capable of inserting primer binding sites for amplification in a random or in an almost random manner can be used in this invention. Examples of such systems include but are not limited to *Staphylococcus aureus* Tn552 (Colegio O R et al., J. Bacteriol., 183: 2384-8, 2001; Kirby C et al., Mol Microbiol., 43: 173-86, 2002), Ty1 (Devine S E, and Boeke J D., Nucleic Acids Res., 22: 3765-72, 1994 and International Patent Application No. WO 95/23875), Transposon Tn7 (Craig, N L, Science. 271: 1512, 1996; Craig, N L, Review in: Curr Top Microbiol Immunol., 204: 27-48, 1996), Tn10 and IS10 (Kleckner N, et al., Curr Top Microbiol Immunol., 204: 49-82, 1996), Mariner transposase (Lampe D J, et al., EMBO J., 15: 5470-9, 1996), Tc1 (Plasterk R H, Curr Top Microbiol Immunol, 204: 125-43, 1996), P Element (Gloor, G B, Methods Mol. Biol., 260: 97-114, 2004), Tn3 (Ichikawa H, and Ohtsubo E., J Biol. Chem. 265: 18829-32, 1990), bacterial insertion sequences (Ohtsubo, F and Sekine, Y, Curr. Top. Microbiol. Immunol., 204: 1-26, 1996), retroviruses (Brown P O, et al., Proc Natl Acad Sci USA, 86: 2525-9, 1989), and retrotransposon of yeast (Boeke J D and Corces V G, Annu Rev Microbiol., 43: 403-34, 1989).

The method for inserting a transposon into a target sequence can be carried out in vitro using any suitable transposon system for which a suitable in vitro transposition system is available or that can be developed based on knowledge in the art. In general, a suitable in vitro transposition system requires, at a minimum, a transposase enzyme and a transposon with transposon end sequences with which the transposase forms a complex in order to catalyze the transposition reaction. Suitable transposase end sequences that can be used in the invention include but are not limited to wild-type, derivative or mutant transposon end sequences that form a complex with a transposase chosen from among a wild-type, derivative or mutant form of a Tn5-type transposase, MuA-type transposase, Tn552-type transposase, Ty1-type transposase, Tn7-type transposase, Tn10-type transposase or IS10-type transposase, Tc1-type transposase, Tn3-type transposase, a P-element-type transposase, a Mariner-type transposase, a Sleeping Beauty-type transposase or any other transposase for which conditions for in vitro transposition are known or subsequently developed. Transposon end sequences recognized by wild-type or mutant forms of Tn5 transposase or MuA transposase are preferred, and those transposon end sequences that result in the highest transposition efficiencies when complexed with the transposase, together with the corresponding optimally active transposase enzymes that complex with them, are most preferred for embodiments of the present invention. Preferably, a transposon is chosen wherein the transposase end sequence required by the transposase for transposition is not too large and the transposon end sequences are of the minimal size possible that function well for the intended purpose, especially for embodiments in which the transposon end sequences are translated to yield additional amino acids attached to a polypeptide encoded by a truncated target nucleic acid. By way of example, the transposon end sequences of the Tn5-derived EZ-Tn5™ Transposon end sequences comprise only 19 nucleotides, whereas some other transposases require much larger end sequences for transposition.

In addition to the transposon end sequences, a transposon of the present invention preferably also comprises a selectable marker, such as but not limited to an antibiotic resistance gene, and an origin of replication (or "ori") that will permit replication of a circular DNA molecule that contains the ori in a suitable microbial host cell, such as but not limited to an *E. coli* cell. In contrast to wild-type transposons, a transposon of the present invention typically does not comprise a gene that encodes the transposase gene that catalyzes its own transposition because transposon that lack the transposase gene are stable once they are inserted into a target sequence, unless they are again contacted with a transposase that binds to the transposon recognition sequences of the inserted transposon. Suitable in vitro transposition systems that can be used to insert a transposon into a target nucleic acid sequence include, but are not limited to, those that use the EZ-Tn5™ hyperactive Tn5 Transposase available from EPICENTRE Technologies, Madison, Wis., or the HyperMu™ Hyperactive MuA Transposase from EPICENTRE or another MuA Transposase, such as that available from Finnzymes Oy, Espoo, Finland, or a Tn7 Transposase, such as that available from New England Biolabs, Beverly, Mass. Transposons of the invention can be made which have the features described in the specifications herein based on information available from the respective vendors or using information well known in the art. By way of example but not of limitation, transposition can be carried out with hyperactive EZ-Tn5™ Tn5-type transposase using transposons made with an EZ-Tn5™ pMOD™-2<MCS> or an EZ-Tn5™ pMOD™-3<R6Kγori/MCS> Transposon Construction Vector, according to the instructions of the manufacturer (EPICENTRE, Madison, Wis.).

The insertion of a transposon into a target sequence according to the present invention can also be carried out in vivo. If transposition is carried out in vivo, transposition into the target sequence is preferably obtained by electroporating a synaptic complex of a transposase and a suitable transposon into the host cell, followed by selection of insertion mutants on medium that selects for the selectable marker encoded by the transposon, as described in U.S. Pat. Nos. 6,159,736 and 6,294,385. This transposition method is exemplified by employing a transposition complex formed by a hyperactive Tn5 transposase and a suitable Tn5-type transposon (Goryshin, I. and Reznikoff, W. S., J. Biol. Chem., 273: 7367, 1998) or a transposition complex formed by HyperMu™ Hyperactive MuA Transposase (EPICENTRE, Madison, Wis.) and a suitable Mu transposon having the R1 and R2 end sequences recognized by the transposase. Suitable synaptic complexes or "Transposome™" complexes (EPICENTRE) between a transposon and a transposase can be made as described in U.S. Pat. No. 6,159,736 and related patents of Goryshin and Reznikoff, or as described in product literature for Tn5-type EZ-Tn5™ Transposome™ complexes or for HyperMu™ MuA Transposome™ complexes from EPICENTRE Technologies, Madison, Wis. The invention is not limited to the use of a synaptic complex to obtain transposition of a target sequence in vivo and other methods of in vivo transposition can also be used. By way of example but without limitation, a plasposon system (Dennis J J and Zylstra G J, Appl. Environ. Microbiol. 64: 2710-2715, 1998) can also be used to obtain transposon insertions of a target sequence in vivo.

After obtaining random insertions into the target sequence, the next step of an embodiment of the invention for obtaining directionally truncated polypeptides comprises amplifying the target nucleic acid into which the transposon has inserted to obtain an amplification product that is delimited by a first primer that anneals selectively to one strand of the target nucleic acid and a second primer that anneals selectively to the transposon in an opposite polarity to the first primer.

The first primer can be thought of as an "anchored primer" which means a DNA primer having a sequence complementary to the known sequence in the target DNA or if the target DNA is part of a vector, complementary to the known sequence in the vector adjacent to the insertion site of the target DNA. The second primer used within the present invention is intended to mean a primer having a sequence complementary to a sequence of the transposon DNA.

The use of the second primer in the amplification reaction results in specific amplification products varying in size, each size representing one deletion of the target DNA.

Thus, the amplification product obtained using the two primers comprises a unidirectionally-truncated target nucleic acid comprising nucleic acid sequences from the target nucleic acid and from the transposon.

In some embodiments of the invention, an RNA polymerase promoter sequence for transcription and a ribosome binding site and a translation start codon for translation are encoded by a nucleic acid sequence in the transposon that are amplified during the amplification step.

In other embodiments, an RNA polymerase promoter sequence for transcription and a ribosome binding site and a translation start codon for translation are encoded by a nucleic acid sequence in a tail or flap portion at the 5'-end of the second amplification primer that anneals to a portion of the transposon that is inserted into the target sequence.

In some embodiments, an RNA polymerase promoter sequence for transcription and a ribosome binding site and a translation start codon for translation are encoded by a nucleic acid sequence from the target nucleic acid that is amplified during the amplification step of the method of the invention. These embodiments are rare because a directionally truncated polypeptide can only be obtained in vivo when an RNA polymerase that is expressible in the host cell can recognize a promoter in the amplified target nucleic acid that is upstream of the target sequence and initiate transcription therefrom and when the ribosome binding site and other translation enzymes are active in translating a transcript that is synthesized in the host cell.

In general, amplification is obtained using the polymerase chain reaction (i.e., PCR). A wide variety of enzymes and kits are available for performing the amplification reaction by PCR. By way of example, but without limitation, the amplification can be performed using either the FailSafe™ PCR System or the MasterAmp™ Extra-Long PCR System from EPICENTRE Technologies, Madison, Wis., as described by the manufacturer. These systems permit rapid optimization of the PCR reaction conditions using a series of 2×PCR Pre-Mixes provided with each system to identify the optimal PreMix for a particular template and primer pair. However, the invention is not limited to the use of these products or conditions for the amplification reaction and any suitable DNA polymerase and reaction mixture that permits amplification of the sequence between the primer that anneals to the target sequence and the primer that anneals to the transposon can be used.

Oligonucleotides for use as amplification primers, including oligonucleotides with modified bases, sugars, or internucleoside linkages, are commercially available and can be purchased from various sources (e.g., TriLink Biotechnologies, San Diego, Calif., USA or Integrated DNA Technologies, Coralville, Iowa). Modified nucleotides are useful for particular purposes, such as alpha-thionucleotides, which are resistant to cleavage by some nucleases. A portion of one or more primers used for amplification can comprise a "tail" or "flap" at the 5'-end that does not anneal to a portion of target sequence or to a portion of a transposon. A "portion" or "region," which can be used interchangeably herein, of an oligonucleotide or polynucleotide is a contiguous sequence of 2 or more bases. A portion can comprise at least about any of 3, 5, 10, 15, 20, 25, 30, 40, 50, 60 70, 80, 90 or 100 contiguous nucleotides.

At least the 3'-portion of an amplification primer is complementary to and hybridizes with or anneals to a sequence of another nucleic acid, such as a target sequence or a sequence in a transposon. The terms "hybridize" and "anneal" or "hybridization" and "annealing" refer to the formation of complexes between nucleotide sequences that are sufficiently complementary to form complexes via Watson-Crick base pairing. With respect to the present invention, nucleic acid sequences that "hybridize" or "anneal" with each other should form "hybrids" that are sufficiently stable to serve the intended purpose. By way of example, but not of limitation, where a primer or a "tailed" primer hybridizes or anneals with a target nucleic acid sequence, each respective hybrid should be sufficiently stable to serve the respective priming functions required for a DNA polymerase to extend the 3'-end of the primer and to copy the target sequence by primer extension of the annealed primer using the target sequence as a template.

The invention is also not limited to the use of PCR to amplify the sequence delimited by the two primers so long as the amplification method used amplifies the same sequence and the amount of amplification product is sufficient for subsequent steps of the method of the invention.

Following amplification of the sequence delimited by the two primers, the next step of a preferred embodiment of the invention for obtaining directionally truncated polypeptides comprises ligating the amplification product to obtain a circular amplification product.

In order to facilitate and improve the efficiency of ligation, the products of the amplification reaction can be "end-repaired," by which is meant that the DNA ends are rendered blunt and, if they do not already have a 5'-phosphate group, the 5'-ends of the amplification product are phosphorylated using a kinase, such as but not limited to, T4 polynucleotide kinase. The amplification products can be end-repaired using the End-It™ DNA End Repair Kit as described by the manufacturer (EPICENTRE Technologies, Madison, Wis., USA).

The end-repaired amplification products are ligated to form circular amplification products, which can be done using a FastLink™ DNA Ligation Kit available from EPICENTRE Technologies, Madison, Wis., according to the directions of the manufacturer. T4 DNA Ligase (available from EPICENTRE) can also be used. Still further, the invention is not limited to the use of the FastLink kit or T4 DNA ligase for the ligation step. As used herein, "ligation" refers to the joining of a 5'-end of a nucleic acid molecule to its 3'-hydroxyl end using a "ligase." In some embodiments of the invention, ligation is effected by a type I topoisomerase moiety attached to one end of a nucleic acid (see U.S. Pat. No. 5,766,891, incorporated herein by reference). Chemical methods of ligation have also been developed and are within the scope of the present invention. The terms "ligating," "ligation," and "ligase" are used in a general sense with respect to describing the invention, and are meant to comprise any suitable method and composition that results in circularization of an amplification product by joining its 5'-end to its 3'-end.

The next step of a preferred embodiment of the invention for obtaining directionally truncated polypeptides comprises transforming the circular self-ligated DNA amplification products into host cells in which the gene for the selectable marker is expressible and in which the circular amplification products are capable of replicating using the origin of replication from the transposon. By way of example but not of limitation, the origin of replication can be an R6Kγ origin of replication and the host cells in which the circular amplification products replicate can comprise cells that express the pir gene product. A host cell strain that expresses the pir gene product that can be used is TranforMax™ EC100D™ pir116 E. coli, which is commercially available from EPICENTRE Technologies, Madison, Wis.

The next step of a preferred embodiment of the invention for obtaining directionally truncated polypeptides comprises selecting host cells that contain the selectable marker encoded by nucleic acid sequences from the transposon that are in the circular amplification product. Selection of host cell transformants that grow on medium that contains a chemical substance to which the selectable marker encodes resistance permits cloning of one circular amplification product per transformant cell, each of which replicates in a host cell using the ori from the transposon and results in a colony comprising a "clone" of a single directionally truncated target sequence that encodes a single directionally truncated polypeptide.

The selectable marker can comprise one or more genes that encodes resistance to toxicity by a chemical substance, such as but not limited to an antibiotic, for which one or more resistance genes from any source that is/are expressible in the host cell is/are known and can be obtained. By way of example, but without limitation, a gene or genes that encodes resistance to an antibiotic, including but not limited to kanamycin, neomycin, ampicillin or another penicillin, tetracycline, chloramphenicol, or trimethoprim, can be used as selectable markers in transposons of the invention, in which case the corresponding antibiotic for which resistance is encoded by the gene is used for selection of the host cells transformed by the circular amplification product. Preferably, the selectable marker encodes a single gene that encodes resistance to a chemical substance. Preferably, the gene or genes that encode the selectable marker are as small as possible in order to minimize the size of the transposon. This is because the potential size of the truncated target sequence comprising the amplification product is reduced as the size of the transposon that is amplified becomes larger (due to the size limits for amplification products that can be obtained using current amplification methods). In embodiments comprising in vivo transposition of host cells, the transformation efficiency of the host cells and the transposition efficiency by the Transposome™ complex can also decrease as the size of the transposon increases. Therefore, it is preferable to keep the transposon as small as possible while providing all of the desired features for the intended purpose.

The origin of replication that permits replication of the transformed circular amplification product comprising the transposon can be any ori known in the art for which the host cell used has or can be made to have expressible genes for proteins and other factors that are required for effective replication from the respective ori. By way of example but not of limitation, a suitable ori that can be used for $E.$ $coli$ includes but is not limited to an R6Kγ-type ori, a colE1-type ori, a p15A ori, or oriV, in which case the host cell will have expressible genes for proteins or other factors required for replication from the respective ori, such as but not limited to an expressible pir gene in embodiments that use the R6Kγori or an expressible trfA gene in embodiments that use oriV. One factor in choosing a suitable ori is size. If the ori is very large or requires expression of many proteins or factors in the host cell to support replication, a larger transposon will be required or it will be more difficult to obtain a suitable host cell. Preferably, the ori sequence in a transposon comprises less than about 300 to about 1000 nucleotides since the potential size of the truncated target sequence comprising the amplification product is reduced as the ori sequence becomes larger (due to the size limits for amplification products that can be obtained using current amplification methods).

The next steps of preferred embodiments of the invention for obtaining a directionally truncated polypeptide comprises obtaining transcription of a directionally-truncated target nucleic acid encoded by a host cell that is selected as containing a replicating circular amplification product and obtaining translation of the resulting transcript.

It is well known in the art that a target sequence can be transcribed if a target sequence that is downstream of a transcription promoter, such as but not limited to a T7-type RNA polymerase (RNAP) promoter, is incubated under transcription conditions with an RNAP that recognizes the respective promoter, either in vitro using a cell-free system, or in vivo in a host cell that can express the RNA polymerase (e.g., see Studier, F W et al., pp. 60-89 in Methods in Enzymology, Vol. 185, ed. by Goeddel, D V, Academic Press, 1990, incorporated herein by reference). The invention is not limited with respect to the RNAP used for transcription. Transcription steps of a method of the invention can use any RNAP for which a suitable promoter sequence that permits transcription with high specificity is known or can be obtained.

In certain embodiments of the invention, promoter sequences may be used that that are recognized specifically by a DNA-dependent RNAP, such as, but not limited to, those described by Chamberlin and Ryan, In: The Enzymes. San Diego, Calif., Academic Press, 15: 87-108, 1982, and by Jorgensen et al., J. Biol. Chem. 266: 645-655, 1991. Several RNAP promoter sequences are especially useful, including, but not limited to, promoters derived from SP6 (e.g., Zhou and Doetsch, Proc. Nat. Acad. Sci. USA 90: 6601-6605, 1993), T7 (e.g., Martin, and Coleman, Biochemistry 26:2690-2696, 1987) and T3 (e.g., McGraw et al., Nucl. Acid. Res. 13: 6753-6766, 1985). An RNAP promoter sequence derived from $Thermus$ $thermophilus$ can also be used (see, e.g., Wendt et al., Eur. J. Biochem. 191: 467-472, 1990; Faraldo et al., J. Bact. 174: 7458-7462, 1992; Hartmann et al., Biochem. 69: 1097-1104, 1987; Hartmann et al., Nucl. Acids Res. 19: 5957-5964, 1991). The length of the promoter sequence will vary depending upon the promoter chosen. For example, the T7 RNAP promoter can be only about 25 bases in length and act as a functional promoter, while other promoter sequences require 50 or more bases to provide a functional promoter.

In preferred embodiments of the invention, the promoter used is a wild-type or mutant promoter sequence that is recognized by an RNAP from a T7-type or T7-like bacteriophage. The genetic organization of all T7-type phages that have been examined has been found to be essentially the same as that of T7. Examples of T7-type phages according to the present invention include, but are not limited to $Escherichia$ $coli$ phages T3, ΦI, ΦII, W31, H, Y, A1, 122, cro, C21, C22, and C23; $Pseudomonas$ $putida$ phage gh-1; $Salmonella$ $typhimurium$ phage SP6; $Serratia$ $marcescens$ phages IV; $Citrobacter$ phage ViIII; and $Klebsiella$ phage No. 11 (Hausmann, Current Topics in Microbiology and Immunology, 75: 77-109, 1976; Korsten et al., J. Gen. Virol., 43: 57-73, 1975; Dunn, et al., Nature New Biology, 230: 94-96, 1971; Towle, et al., J. Biol. Chem., 250: 1723-1733, 1975; Butler and Chamberlin, J. Biol. Chem., 257: 5772-5778, 1982). Mitochondrial RNAPs have also been found to be similar to those of T7-type phages and therefore are considered to be of a "T7-type" herein. By "T7-type RNAP" we mean an RNAP from T7-type phages T7, T3, SP6, ΦI, ΦII, W31, H, Y, A1, 122, cro, C21, C22, and C23; gh-1, IV, ViIII or 11, or a mitochondrial RNAP, as well as derivative and mutant forms of these RNAPs, and a "T7-type RNAP promoter" is a promoter from which transcription is initiated by the cognate T7-type RNAP (Studier, F W. et al., ibid). Preferred T7-type RNAPs of the invention comprise T7 RNAP, T3 RNAP and SP6 RNAP and the preferred promoter is one from which the respective RNAP specifically initiates transcription.

Promoters of the invention can also comprise single-stranded pseudopromoters or synthetic promoters that are recognized by an RNA so as to function in a method of the invention. A "pseudopromoter" or "synthetic promoter" of the present invention can be any single-stranded sequence that is identified and/or selected to be functional as a promoter for in vitro transcription by an RNAP that binds the promoter with specificity and functions as a promoter for the RNAP in a transcription reaction. If a pseudopromoter or synthetic promoter is used as a promoter in any method of the invention, then the corresponding RNAP for which the pseudopromoter or synthetic promoter was identified and/or selected is used in the method. By way of example, but not of limitation, a promoter comprising a ssDNA pseudopromoter can be obtained as described by Ohmichi et al. (Proc. Natl. Acad. Sci. USA 99:54-59, 2002, incorporated herein by reference) and used for a method of the invention that uses $E.$ $coli$ RNAP or a T7-type phage RNAP.

Some embodiments of the invention also comprise use of the coliphage N4 RNAP (N4 vRNAP) (Rothman-Denes, L. B., and Schito, G. C., Virology, 60: 65-72, 1974; Falco, S. C. et al., Proc. Natl. Acad. Sci. USA, 74: 520-523, 1977; Falco, S. C. et al., J. Biol. Chem., 255: 4339-4347, 1980; Kazmierczak, K. M., et al., EMBO J., 21: 5815-5823, 2002) and the promoter sequences of said ssDNA oligos comprise a conserved promoter sequence recognized by the $Escherichia$ $coli$ phage N4 vRNAP, wherein said promoter sequence comprises a 5-basepair stem and 3-base loop hairpin structure (Glucksmann, M. A. et al., Cell, 70: 491-500, 1992; Haynes, L. L. and Rothman-Denes, L. B., Cell, 41: 597-605, 1985). In contrast to other known RNAPs, the N4 vRNAP transcribes single-stranded, promoter-containing templates in vitro with in vivo specificity (Falco, S. C et al., Proc. Natl. Acad. Sci. USA, 75: 3220-3224, 1978; Haynes, L. L. and Rothman-Denes, L. B., Cell, 41: 597-605, 1985). If an N4 vRNAP is used in an embodiment of the invention, the RNAP can comprise a transcriptionally active 1,106-amino acid domain of the N4 vRNAP (designated "mini-vRNAP"), which corresponds to amino acids 998-2103 of N4 vRNAP (U.S. Patent Application No. 2003/0096349; Kazmierczak, K. M., et al., EMBO J., 21: 5815-5823, 2002), and methods and/or reaction conditions for use of this enzyme or strains that contain it are as described therein.

In embodiments of the method in which only one strand of a double-stranded amplification product is needed for replication (e.g., using a single-stranded phage M13 ori), transcription (e.g., using mini-vRNAP), and translation, the amplification step can be performed using one amplification primer with a 5'-phosphorylated end so that circularization of the DNA strand made using this primer will occur during the ligation step to form a single-stranded circular amplification product having a single-stranded promoter joined to a truncated target sequence, and a second primer that lacks a 5'-phosphate so that circularization will not occur during the ligation step. In these embodiments, the ligation can be effected using a double-stranded amplification product and then the amplification product denatured to separate the unligated strand from the ligated strand, or the ligation can be effected using a "ligation splint" comprising an oligonucleotide that anneals to both ends of the strand of the amplification product having a 5'-phosphate, or the ligation can be effected by denaturing the two strands of a double-stranded amplification product and ligating using a non-homologous ligase, such as but not limited to a single-stranded DNA ligase available from Prokaria, Reykjavik, Iceland.

The invention also comprises use of any other RNAP known in the art that functions in a method of the invention using methods and reaction conditions in the public literature that describe use of the enzyme or strains that contain it.

In preferred embodiments of methods of the invention for obtaining a directionally truncated polypeptide, transcription of a circular amplification product comprising a directionally truncated target nucleic acid sequence that replicates in a selected host cell and subsequent translation of the resulting transcript is carried out in vivo in a suitable host cell. In preferred embodiments of this aspect of the invention, the host cell contains an expressible gene for a T7-type RNAP and transcription of the directionally truncated target sequence is initiated from a T7-type RNAP promoter, with T7 RNAP and a respective T7 RNAP promoter being most preferred.

A wide variety of specialized *E. coli* cells are commercially available for in vivo transcription of a target sequence that is downstream of a T7-type promoter and then obtaining in vivo expression of a polypeptide encoded by the resulting transcript encoded by the target sequence. Suitable *E. coli* host cells that can be used for this purpose for the present invention include, but are not limited to, the many *E. coli* strains for expression of proteins from pET vectors that are commercially available from Novagen® EMD Biosciences, Madison, Wis., and from Invitrogen®, Carlsbad, Calif. In general, these *E. coli* strains have an expressible T7 RNA polymerase gene that is inducible by a specific inducing substance and factors that affect translation, which can vary depending on the particular strain and for particular purposes. These *E. coli* strains permit high-level expression of a directionally truncated polypeptide encoded by a directionally truncated target sequence according to the methods of the present invention in a highly controlled manner. Preferably, transcription of the directionally truncated nucleic acid is tightly controlled in the host cell so that transcription and translation of the corresponding directionally truncated polypeptide only occurs under specific and easily-controlled growth conditions.

In other embodiments of the invention, a directionally-truncated polypeptide is obtained by in vitro cell-free transcription of the directionally truncated target nucleic acid sequence and subsequent in vitro translation of the resulting RNA transcript. In preferred embodiments of this embodiment, in vitro transcription is carried out using a T7-type RNA polymerase, and most preferably, in vitro transcription is carried out using T7 RNAP, T3 RNAP or SP6 RNAP.

Kits and enzymes for in vitro transcription are commercially available from many vendors and the appropriate reaction mixtures and conditions for carrying out steps of the present invention comprising in vitro transcription can use those products as described by the manufacturers. By way of example but without limitation, in vitro transcription using T7 RNAP can be carried out using the AmpliScribe™ T7-Flash™ Transcription Kit or the AmpliScribe™ T7 High Yield Transcription Kit from EPICENTRE Technologies, Madison, Wis. as described in the product literature. Similarly, if T3 RNAP or SP6 RNAP is used in a method of the invention for in vitro transcription, an AmpliScribe™ T3-Flash™ High Yield Transcription Kit or with the AmpliScribe™ SP6 High Yield Transcription Kit (EPICENTRE Technologies, Madison, Wis.), respectively, can be used as described.

The invention is not limited to the in vitro reaction conditions or concentrations of reactants referred to above. Those with skill in the art will know that other suitable reaction conditions under which an RNA polymerase of the invention can be used can be found by simple experimentation, and any of these reaction conditions are also included within the scope of the invention. Such media and conditions are known to persons of skill in the art, and are described in various publications, such as U.S. Pat. No. 5,679,512 and PCT Pub. No. WO99/42618, incorporated herein by reference in their entirety.

In embodiments in which a directionally truncated target nucleic acid sequence is transcribed in vitro, a next step of a method of the invention comprises obtaining a directionally truncated polypeptide by in vitro translation of the resulting transcript. Systems and kits for in vitro translation of the RNA transcripts to obtain truncated polypeptides are also commercially available from many sources and can be used for the present invention. By way of example but not of limitation, rabbit reticulocyte lysate, wheat germ extract, and *E. coli* S30 extract systems from Promega Corporation, Madison, Wis. can be used for the present invention. Still further, kits for coupled in vitro transcription and in vitro translation are also commercially available and can be used, such as TNT® Quick Coupled Transcription/Translation Systems from Promega.

Once a directionally truncated polypeptide is translated, either in vivo in a host cell or in vitro in a cell-free system, an optional step of a method of the present invention comprises purifying the directionally-truncated polypeptide to obtain a purified directionally-truncated polypeptide. A wide variety of methods are available in the art for purification of peptides based on size, charge, solubility, and other characteristics of the particular polypeptides and any of these can be used to obtain purified truncated polypeptides according to the methods of the present invention.

In some embodiments of the present invention a transposon end sequence, preferably a Mu transposon end sequence (although functionally equivalent sequences are also preferred), is inserted into a plasmid or other vector which plasmid or other vector comprises an origin of replication and/or a selectable marker as well as a nucleic acid sequence that encodes for a polypeptide. The invention also comprises a method for obtaining a bidirectionally-truncated polypeptide, the method comprising, preferably:

(a) obtaining a first circular amplification product comprising a unidirectionally-truncated target nucleic acid that encodes a unidirectionally-truncated polypeptide using a first transposon according to a method described herein above;

(b) contacting the first circular amplification product obtained in step (a) with a second transposon that encodes a second selectable marker under conditions wherein a transposase binds to the second transposon and catalyzes insertion of the second transposon into the target nucleic acid sequences of the first circular amplification product;

(c) contacting the denatured first circular amplification product into which the second transposon has inserted with a forward primer that anneals selectively to one strand of the first circular amplification product and a reverse primer that anneals selectively to the second transposon in an opposite polarity to the forward primer and incubating under amplification conditions so as to obtain a second amplification product that is delimited by the two primers, wherein the second amplification product comprises nucleic acid sequences of at least a portion of the first transposon at one end of the bidirectionally-truncated target nucleic acid sequence and nucleic acid sequences of at least a portion of the second transposon at the opposite end of the bidirectionally-truncated target nucleic acid sequence;

(d) ligating the second amplification product to obtain a second circular amplification product;

(e) transforming the second circular amplification product into a host cell, wherein the second circular amplification product is replicated and the selectable markers encoded by the first transposon and the second transposon are expressed;

(f) selecting host cells that contain the selectable marker encoded by nucleic acid sequences from the first and second transposons that are in the second circular amplification product;

(g) obtaining an RNA transcript by transcription of the bidirectionally-truncated target nucleic acid encoded by the second circular amplification product;

(h) obtaining a bidirectionally-truncated polypeptide by translation of an RNA transcript from the bidirectionally-truncated target nucleic acid encoded by the second circular amplification product; and (i) optionally, purifying the bidirectionally-truncated polypeptide.

In some embodiments of this method for obtaining a bidirectionally truncated polypeptide, the same transposase is used to catalyze transposition of both the first transposon and the second transposon.

In other embodiments of this method for obtaining a bidirectionally truncated polypeptide, different transposases are used to catalyze transposition of the first and the second transposons.

In embodiments in which different transposases are used to catalyze transposition of the first and the second transposons, the transposase used to catalyze transposition of the first transposon is selected from among a wild-type, mutant or derivative form of a Tn5 transposase, a Tn552 transposase, a Ty1 transposase, a Tn7 transposase, a Tn10 transposase or a IS10 transposase, a Tc1 transposase, a Tn3 transposase, a P-element transposase, a Mariner transposase, a Sleeping Beauty transposase or another transposase and the transposase used to catalyze transposition of the second transposon is a wild-type, mutant or derivative form of MuA transposase.

In other embodiments for obtaining a bidirectionally truncated polypeptide a first and a second transposon are used simultaneously to obtain a bidirectionally truncated polypeptide, e.g. a target nucleic acid is contacted with two different transposons under conditions whereby simultaneous insertion of both transposons into the target nucleic acids occurs, wherein the first transposon encodes a first selectable marker that is expressible in a host cell and an origin of replication that is capable of directing replication in the host cell and wherein the second transposon encodes a second selectable marker.

Still another method for providing a bidirectionally-truncated polypeptide comprises:

(a) obtaining a first circular amplification product comprising a unidirectionally-truncated target nucleic acid that encodes a unidirectionally-truncated polypeptide using a first transposon according to a method described above for obtaining a unidirectionally truncated polypeptide;

(b) contacting the first circular amplification product obtained in step (a) with second transposon end sequences under conditions wherein a transposase binds to the second transposon end sequences and catalyzes insertion of the end sequences into the target nucleic acid sequence of the first circular amplification product;

(c) contacting the denatured first circular amplification product into which second transposon end sequences have inserted with a forward primer that anneals selectively to one strand of the first circular amplification product and a reverse primer that anneals selectively to the second transposon end sequence in an opposite polarity to the forward primer and incubating under amplification conditions so as to obtain a second amplification product that is delimited by the two primers, wherein the second amplification product comprises nucleic acid sequences of at least a portion of the first transposon at one end of the bidirectionally-truncated target nucleic acid sequence and of at least a portion of the second transposon end sequence at the opposite end of the bidirectionally-truncated target nucleic acid sequence;

(d) optionally, separating nucleic acid molecules comprising the first circular amplification product from nucleic acid molecules comprising the second amplification product;

(e) ligating the second amplification product to obtain a second circular amplification product;

(f) transforming the second circular amplification product into a host cell, wherein the second circular amplification product is replicated and the selectable marker encoded by the first transposon is expressed;

(g) selecting host cells that express the selectable marker encoded by the first transposon that is in the second circular amplification product;

(h) obtaining an RNA transcript by transcription of the bidirectionally-truncated target nucleic acid encoded by the second circular amplification product;

(i) obtaining a bidirectionally-truncated polypeptide by translation of the RNA transcript from the bidirectionally-truncated target nucleic acid encoded by the second circular amplification product; and (j) optionally, purifying the bidirectionally-truncated polypeptide.

In one embodiment of this method for obtaining a bidirectionally truncated polypeptide, the same transposase is used to catalyze transposition of both the first transposon and of the transposon end sequences. In such embodiments, it is preferred that the transposase used to catalyze transposition of both the first transposon and of the transposon end sequences is a wild-type or a mutant or derivative of MuA transposase.

In other embodiments of this method for obtaining a bidirectionally truncated polypeptide, different transposases are used to catalyze transposition of the first transposon and of the transposon end sequence. In these embodiments, it is preferred that the transposase used to catalyze transposition of the first transposon is selected from among a wild-type, mutant or derivative form of a Tn5 transposase, a Tn552 transposase, a Ty1 transposase, a Tn7 transposase, a Tn10 transposase or a IS10 transposase, a Tc1 transposase, a Tn3 transposase, a P-element transposase, a Mariner transposase, a Sleeping Beauty transposase or another transposase and the transposase used to catalyze transposition of the second transposon end sequences is a wild-type, mutant or derivative form of MuA transposase.

B. Kits and Compositions of the Invention

The invention also comprises kits and compositions (e.g., reaction mixtures, etc.) for a method of the invention for obtaining unidirectionally or bidirectionally truncated polypeptides. A kit is a combination of individual compositions useful for carrying out one or more steps a method of the invention, wherein the compositions are optimized for use together in the method. A composition comprises an individual component for at least one step of a method of the invention.

By way of example but not of limitation, one embodiment of the invention comprises a kit for obtaining a unidirectionally truncated polypeptide using a method of the invention, the kit comprising one or more of:

(a) a transposon (e.g., comprising one or more of a selectable marker, an origin of replication, a promoter, a ribosome binding site and a translation start codon);

(b) a first primer that anneals (e.g., selectively) to one strand of a target nucleic acid and/or a second primer that anneals (e.g., selectively) to the transposon in an opposite polarity to the first primer;

(c) a thermostable polymerase with or without reaction buffer and nucleotides for amplification using the first primer and the second primer;

(d) a ligase (e.g., for circularizing an end-repaired linear amplification product);

(e) a host cell, for example, in which the selectable marker is expressed and in which can replicate a double-stranded DNA having the ori in the transposon, the host cell also comprising an expressible gene for an RNA polymerase that recognizes the promoter in the transposon for transcription, and that can use a transcription product transcribed from the promoter to translate a polypeptide;

(f) one or more of reaction buffers, cofactors, and other substrates, such as nucleotides, required for reactions using each of the compositions of the invention; and (g) instructions for use of the compositions in the steps of the method.

Those with knowledge in the art will understand that a kit for carrying out a method of the invention can also comprise a subset of the above compositions in any appropriate combination and for any reason, such as to provide the user flexibility to adapt the method to the user's own target sequence, or to permit the user to employ other compositions for any of a variety of reasons. By way of example but not of limitation, a kit can comprise only the primer that anneals to a sequence in the transposon so that the user can supply the primer that anneals to his or her target sequence. By way of further example, a kit of the present invention can comprise all of the above components except the thermostable polymerase, reaction buffer and nucleotides for amplification, and/or the ligase, either or both of which can be obtained from an alternative source.

In some embodiments of a kit of the invention, the second primer comprises a 5'-end that anneals to the translation start site of the transposon.

In some embodiments, the transposon in the kit does not encode a promoter sequence, a ribosome binding site, or a translation start codon and these genetic elements are added to the amplification product by using a promoter primer comprising a flap or tail at the 5'-end that encodes them.

Another kit of the invention can comprise a complex or a Transposome™ complex (EPICENTRE) between a transposase and a transposon, as described herein, for use in embodiments of methods in which the insertion of the transposon into the target sequence in carried out in vivo.

In another embodiment, a kit also comprises compositions for in vitro transcription and in vitro translation for carrying out a method of the invention in which transcription of the circular amplification product and translation of the resulting transcript occur in vitro rather than in vivo in a host cell. Optionally, a kit for a method that comprises in vitro transcription and translation of a truncated polypeptide can also comprise compositions for purification of DNA comprising clones of individual circular amplification products for subsequent in vitro transcription; these DNA purification compositions can be the same as or similar to any composition that is known in the art or that is developed for purifying plasmids from host cells. Many compositions for methods for plasmid purification are known in the art and any of these can comprise a composition or kit of the present invention for purification of clones of circular amplification products from host cells.

Still another kit of the invention comprises, in addition to any of the compositions described above, a transposase and a second transposon or a transposase and second transposon end sequences for use in a method of the invention for obtaining bidirectionally truncated polypeptides.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

Standard recombinant DNA and molecular cloning techniques used here are well known in the art and are described by Sambrook, J., Fritsch, E. F. and Maniatis, T., Molecular Cloning: A Laboratory Manual, Second Edition, Cold Spring Harbor Laboratory Press, Cold Spring Harbor, N.Y. (1989).

Example 1

Random Insertion of a Transposon into a Target DNA

The *E. coli* DNA polymerase I gene (polA) was chosen as target DNA, since it contains three well-characterized domains: a 5'-to-3' exonuclease domain, a 3'-to-5' exonuclease domain, and a DNA polymerase domain (see FIG. 3). Target DNA was prepared by PCR using *E. coli* genomic DNA as a template and the following primers:

```
                         (polFP, Sequence ID No. 1)
5'-CAGGCACGGACATTATGGTT-3'
and (polRP, Sequence ID No. 2)
5'-AGGCATGTTCAGGCGAATCT-3'.
```

A 50-microliter PCR reaction mixture was prepared comprising the two primers, about 100 nanograms of *E. coli* DNA, FailSafe™ DNA Polymerase Mix, and FailSafe™ PCR PreMix E using methods described by the manufacturer (EPICENTRE). Thirty PCR cycles were performed comprising a 30-second denaturation step at 94° C., a 30-second annealing step at 60° C., and a 2.5-minute extension step at 72° C.

The transposon used in this example was derived from the EZ::TN™<R6Kγori/KAN-2> Transposon (commercially available from EPICENTRE Technologies, Madison, Wis.) and was designated EZ::TN™<R6Kγori/KAN-2/T7Exp>. It contains an R6Kγ origin of replication, a kanamycin resistance gene, a start codon (ATG) within the transposon mosaic ends, a T7 RNA polymerase promoter, a lac operator, and a ribosome binding site (RBS) at a distance from the start codon that allows translation to begin at the correct site. EZ::TN™<R6Kγori/KAN-2/T7Exp> is shown in FIG. 2A.

The transposition reaction was carried out as recommended by EPICENTRE for the EZ:TN™<R6Kγori/KAN-2> Insertion Kit, except that the transposon/target ratio was reduced from 1.0 to 0.1 to minimize inter-molecular transposition events between transposons. In particular, a 10-microliter reaction mixture was prepared comprising 200 nanograms of the PCR amplified target DNA, 15 nanograms of the EZ::TN™ R6Kγori/KAN-2/T7Exp> Transposon, EZ:TN™ Transposase, and 10×EZ::TN™ Reaction Buffer. The reaction mixture was incubated at 37° C. for 2 hours, and then one microliter of 1% SDS was added, followed by heating at 70° C. for 10 minutes to stop the reaction.

Example 2

Amplification of a Portion of the Target Sequence and a Portion of the Inserted Transposon The products of the transposition reaction obtained in EXAMPLE 1 were ethanol precipitated to remove SDS, diluted 1:10 with TE, and subjected to PCR using the FailSafe™ PCR system with FailSafe™ PCR PreMix E, which is commercially available from EPICENTRE Technologies, Madison, Wis. Twenty-five PCR cycles were performed comprising a 30-second denaturation step at 94° C., a 30-second annealing step at 60° C., and a 4-minute extension step at 72° C.

The primers used were polRP (Sequence ID No. 2) and the transposon end primer (RPX, Sequence ID No. 3):

```
                        (RPX, Sequence ID No. 3)
5'-AGATGTAGGTGTTCCACAGGGTAG-3'.
```

Example 3

Cloning of the Amplification Products

The products of the PCR reaction of EXAMPLE 2 were precipitated with an equal volume of PCR precipitation solution (EPICENTRE), resuspended in 50 microliters of TE (10 mM Tris, 1 mM EDTA, pH 7.5), end-repaired with the End-It™ DNA End-Repair-Kit (commercially available from EPICENTRE Technologies, Madison, Wis.), and self-ligated using the FastLink™ DNA Ligation Kit (EPICENTRE, Madison, Wis.). One microliter of the ligated DNA was electroporated into electrocompetent TransforMax™ EC100D™pir116:λDE3 cells. This TransforMax™ EC100D™pir116:λDE3 host strain was prepared from the TransforMax™ EC100D™pir116 strain (available from EPICENTRE) by using the λDE3 Lysogenization Kit (commercially available from Novagen®, EMD Biosciences, Madison, Wis.) as described by Novagen; λDE3 lysogenization incorporates an inducible T7 RNA polymerase gene into the TransforMax™ EC100D™pir116 strain, which can be used to express genes in the resulting host cells that are under the control of a T7 RNA polymerase promoter.

Following electroporation and growth of the host cells on plates containing the antibiotic for which resistance is encoded by the selectable marker of the transposon (e.g., 50 micrograms of kanamycin per ml of medium), antibiotic-resistant colonies were screened for clone size by colony PCR using as primers polRP (Sequence ID No. 2) and RPX (Sequence ID No. 3). The results are shown in FIG. 4. Based on the screening results, colony PCR products ranging in size from about 2 to 4.8 kilo basepairs were chosen and subsequently sequenced to determine the exact transposon insertion point and the reading frame. One-third of the clones were expected to be in-frame with the target DNA.

Multiple clones were obtained comprising in-frame transposon insertion points. The insertion points for a number of such clones are shown by the downward arrows in FIG. 3. These finding illustrate that the transposition reaction and the DNA amplification reaction resulted in truncated target sequences.

Example 4

Expression of the Amplification Products

Some of the clones obtained in EXAMPLE 3 were selected and grown in culture. After the culture reached the mid-log growth phase, protein expression was induced with one microliter of 0.4 M IPTG per milliliter of culture. After 2 additional hours of growth at 37° C., the cultures were harvested and lysed following standard microbiology procedures. The expression of truncated *E. Coli* DNA polymerase I proteins (PolI) was examined by SDS-PAGE to determine if proteins of the expected sizes had been made.

All examined clones express proteins of the expected sizes including PolI truncation clone 2, for which the results are shown in FIG. 5. This indicates that uni-directional N-terminal amino-end deletions of the DNA polymerase I protein were synthesized.

Example 5

Functional Analysis of Truncated Polypeptides

The DNA polymerase activities of truncated PolI proteins obtained in EXAMPLE 4 were analyzed by in-gel protein renaturation and reaction with poly d(A-T) substrate. Samples were run on polyacrylamide gels containing 0.2 micrograms per milliliter poly d(A-T). After electrophoresis, the gels were soaked in three changes of protein purification buffer to remove SDS and allow for protein renaturation. The gels were incubated overnight at 37° C. in 20 milliliters of purification buffer containing 0.2 mM dATP and 0.2 mM dTTP. The gels were stained with SYBR® Gold (Molecular Probes, Eugene, Oreg.) to visualize bands of DNA synthesis.

The results show that the PolI truncation clone 2 (for which the size of the truncated target DNA is indicated in FIG. 3) produces a DNA band that is very similar to, but slightly larger than that produced by a Klenow fragment (DNA polymerase I lacking the 5'-to-3' exonuclease domain). Therefore, the protein produced by PolI truncation clone 2 functions as one would expect based on the fact that its transposon insertion site suggests that it is slightly larger than the Klenow fragment.

Further results for PolI truncation clones A5 and 5 (for which the insertion sites of those clones are illustrated by downward arrows in FIG. 3) did not reveal any polymerase activity of the truncated proteins produced by those clones, even though they contain the entire polymerase domain. This surprising finding suggests that the 3'-to-5' exonuclease domain might play a critical role within the folding process of the functional protein. These results indicate that the methods of the present invention can be used to conduct functional analyses of proteins and protein domains leading to unexpected results.

Example 6

Subsequent Deletion of the Truncated Target Sequence at the Other End by Insertion of a Second Transposon Two of the PolI truncation clones obtained in EXAMPLE 3, clones 2 and 5, were used as targets to insert a different transposon type, a Mu transposon. In this example the HyperMU™ <CHL-1> Transposon, which is commercially available from EPICENTRE, was used. A 20-microliter reaction mixture was prepared comprising about 300 nanograms plasmid DNA isolated from clones 2 and 5, 10 nanograms HyperMu™ <CHL-1> Transposon, HyperMu™ Transposase (EPICENTRE), and HyperMu™ 10× Reaction Buffer (EPICENTRE). The reaction mixture was incubated for 2 hours at 37° C., and then one microliter of 1% SDS was added, followed by heating at 70° C. for 10 minutes to stop the reaction.

The products of the transposition reaction obtained were ethanol precipitated to remove SDS, diluted 1:10 with TE, and subjected to PCR using the FailSafe™ PCR System with FailSafe™ PCR PreMix E, which is commercially available from EPICENTRE Technologies, Madison, Wis. Twenty-five PCR cycles were performed comprising a 30-second denaturation step at 94° C., a 30-second annealing step at 60° C., and a 4-minute extension step at 72° C. The primers used were RPX (Sequence ID No. 3) and MuRPX (Sequence ID No. 4):

```
                              (MuRPX, Sequence ID No. 4)
5'-GGATCCTGTCTCAAAATCTCTG-3'.
```

Subsequently, the PCR products were purified and cloned following the same procedures as described in EXAMPLE 3; chloramphenicol-resistant colonies, presumably containing a portion of the HyperMu <CHL-1> Transposon, were selected on medium containing 12.5 micrograms of chloramphenicol per milliliter. The obtained kanamycin- and chloramphenicol-resistant clones were screened for size by colony PCR and selected clones were sequenced to determine the insertion points of the Mu transposon.

The experiment resulted in clones for unidirectional carboxyl-end truncations in addition to the previously obtained clones for unidirectional amino-end truncations. The insertion points of these clones are illustrated in FIG. 3 as upward arrows. The combination of two different transposition systems enables the synthesis of bidirectionally truncated proteins, with truncations from both the amino and the carboxyl ends.

Example 7

Subsequent Deletion of the Truncated Target Sequence at the Other End by Insertion of Transposon End Sequences The generation of unidirectional carboxyl-end truncations illustrated in Example 6 was accomplished using transposon end sequences instead of a complete second transposon.

Mu-end transposo ends ("Mu-ends") were formed by annealing two synthetic oligonucleotide sequences that correspond to the Mu inverted repeat region containing the R1 and R2 recognition sequences for MuA transposase. Specifically, equal volumes of 50 micromolar solutions of a 51 nt oligonucleotide (Sequence ID No. 5) and a 56 nt oligonucleotide (Sequence ID No. 6) were mixed and annealed to each other, resulting in a 51 bp double-stranded Mu-end containing a 5 nt overhang at the 5'-end. When combined with MuA transposase, this Mu-end was transposed into a target DNA in the same manner as a complete transposon.

5'-

```
                                  (Sequence ID No. 5)
5'-CGTTTTCGCATTTATCGTGAAACGCTTTCGCGTTTTTCGTGCGCCG
CTTCA-3'
```

5'-

```
                                  (Sequence ID No. 6)
5'-AGATCTGAAGCGGCGCACGAAAAACGCGAAAGTGTTTCACGATAAA
TGCGAAAACG-3'.
```

A 20 microliter reaction mixture was prepared comprising about 300 nanograms of plasmid DNA isolated from clone 2, an equimolar amount of Mu-ends, HyperMU™ Transposase (EPICENTRE) and HyperMu 10× Reaction Buffer (EPICENTRE). The reaction mixture was incubated for 2 hours at 37° C., and then one microliter of 1% SDS was added, followed by heating at 70° C. for 10 minutes to stop the reaction.

The products of the transposition reaction obtained were ethanol precipitated to remove SDS, diluted 1:10 with TE, and subjected to PCR using the FailSafe™ PCR System with FailSafe™ PCR PreMix E, which is commercially available from EPICENTRE Technologies, Madison, Wis. Twenty-five PCR cycles were performed comprising a 30-second denaturation step at 94° C., a 30-second annealing step at 60° C., and a 4-minute extension step at 72° C. The primers used were RPX (Sequence ID No. 3) and Mu-1 RP-1 (Sequence ID No. 7):

```
                             (Mu-1 RP-1, Sequence ID No. 7)
    5'-TCGCGTTTTTAGTTCACCGCTTCA-3'.
```

The sequence of the Mu-end primer (Mu-1 RP-1, Sequence ID No. 7) was different from the corresponding sequence of the Mu-end at several positions, which differences resulted in the PCR products comprising inserted Mu-end sequences that contained translation stop codons in all three reading frames.

Subsequently, the PCR products were purified and cloned following the same procedure as described in EXAMPLE 3.

Kanamycin-resistant clones were screened by colony PCR and selected clones were sequenced to determine the insertion points of the Mu-ends.

Although there was no antibiotic selection for Mu-end insertion, the PCR amplification process resulted in the majority of clones containing Mu-end sequences.

As a consequence of the introduction of translation stop codons into the Mu-end sequences of the PCR products as described above, the obtained carboxyl-end truncations contained only 0, 3 or 5 additional amino acids encoded by the Mu-end sequence.

Example 8

Making Truncated Target Sequences from Genomic DNA

A transposition reaction was carried out using total *E. coli* genomic DNA as a target for a transposon insertion reaction. The HyperMu™ <R6Kγori/KAN-1> Transposon, which is commercially available from EPICENTRE, Madison, Wis., was used. A 20-microliter reaction mixture was prepared comprising about 500 nanograms *E. coli* genomic DNA, 25 nanograms HyperMu™ <R6Kγori/KAN-1> Transposon, HyperMU™ Transposase (EPICENTRE), and HyperMu™ 10× Reaction Buffer (EPICENTRE). The reaction mixture was incubated for 2 hours at 37° C., and then 2 microliters of 1% SDS was added, followed by heating at 70° C. for 10 minutes to stop the reaction.

The products of the transposition reaction obtained were ethanol precipitated to remove SDS, diluted 1:10 with TE, and subjected to PCR using the FailSafe™ PCR system with FailSafe™ PCR PreMix E, which is commercially available from EPICENTRE Technologies, Madison, Wis. The primers used were MuRPX (Sequence ID No. 4) and polFP (Sequence ID No. 1). Twenty-five PCR cycles were performed comprising a 30-second denaturation step at 94° C., a 30-second annealing step at 60° C., and a 7-minute extension step at 72° C.

Unidirectionally truncated polI sequences were obtained, illustrating that the present invention provides methods that are highly sensitive and allow the use of bacterial genomic DNA to generate truncated target sequences and truncated polypeptides.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

We claim:

1. A method for generating a host cell transformed with an amplification product encoding a directionally truncated polypeptide, the method comprising:
   (a) providing: i) a double-stranded target nucleic acid molecule, ii) host cells, and iii) a separate transposon comprising an origin of replication capable of directing replication in the host cells;
   (b) contacting said target nucleic acid molecule with said transposon under conditions wherein insertion of said transposon into said target nucleic acid molecule occurs, thereby generating a transposon-containing target nucleic acid molecule;
   (c) amplifying the transposon-containing target nucleic acid molecule by PCR using a first primer that anneals to a target sequence in said target nucleic acid molecule that encodes a polypeptide from which it is desired to generate a directionally truncated polypeptide and a second primer that anneals to said transposon in an opposite polarity to said first primer to generate amplification products that are delimited by said first and second primer, wherein each amplification product comprises at least a portion of the sequence from said transposon, wherein said portion includes the origin of replication, and at least a truncated portion of, and no more than a truncation portion of, said target sequence in said target nucleic acid molecule;
   (d) ligating said amplification products so that each amplification product is ligated to itself to generate a circular amplification product;
   (e) transforming said circular amplification products into host cells, wherein each said circular amplification product is replicated in a host cell using said origin of replication of said transposon; and
   (f) selecting a host cell that contains a replicated circular amplification product that encodes a directionally truncated polypeptide from among the host cells transformed in step (e).

2. The method of claim 1, further comprising the step of generating a directionally truncated polypeptide in said host cells.

3. The method of claim 2, wherein said directionally truncated polypeptide is a unidirectionally truncated polypeptide.

4. The method of claim 2, wherein said directionally truncated polypeptide is a bidirectionally truncated polypeptide.

5. The method of claim 1, wherein said transposon comprises a selectable marker, wherein step (f) of selecting host cells that contains said replicated circular amplification product comprises selecting host cells that contain said selectable marker.

6. The method of claim 1, further comprising the step of obtaining an RNA transcript by transcription of said truncated portion of said target nucleic acid encoded by said replicated circular amplification product.

7. The method of claim 2, further comprising the step of purifying said directionally truncated polypeptide.

8. The method of claim 1 wherein step (b) is carried out in vitro.

9. The method of claim 1 wherein step (b) is carried out in vivo.

10. The method of claim 6 wherein the step of obtaining an RNA transcript by transcription of said truncated portion of said target nucleic acid encoded by said replicated circular amplification product is carried out in vivo in the host cells.

11. The method of claim 2, wherein the host cell contains an expressible gene for a 17-type RNA polymerase and the step of generating a directionally truncated polypeptide in said host cell comprises inducing said 17-type RNA polymerase in said host cells.

12. The method of claim 1, wherein the host cells contain an expressible gene for an RNA polymerase selected from the group consisting of T7 RNA polymerase, T3 RNA polymerase and SP6 RNA polymerase.

13. The method of claim 6 wherein the step of obtaining an RNA transcript by transcription of said truncated portion of said target nucleic acid encoded by said replicated circular amplification product is carried out in vitro using cell-free transcription.

14. The method of claim 13 wherein in vitro transcription is carried out using a T7-type RNA polymerase.

15. The method of claim 13 wherein in vitro transcription is carried out using an RNA polymerase selected from the group consisting of T7 RNA polymerase, T3 RNA polymerase and SP6 RNA polymerase.

16. The method of claim 1, further comprising generating a directionally truncated polypeptide in vitro using cell-free transcription and translation.

17. The method of claim 6 wherein an RNA polymerase for said transcription uses an RNA polymerase promoter encoded by a nucleic acid sequence in said transposon that is contained in said replicated circular amplification product.

18. The method of claim 17 wherein the RNA polymerase promoter is a promoter for a T7-type RNA polymerase.

19. The method of claim 17 wherein the RNA polymerase promoter is selected from the group consisting of a promoter for T7 RNA polymerase, T3 RNA polymerase and SP6 RNA polymerase.

20. The method of claim 6 wherein an RNA polymerase for said transcription uses an RNA polymerase promoter encoded by a nucleic acid sequence in a primer used for said amplifying.

21. The method of claim 20 wherein the RNA polymerase promoter is a promoter for a T7-type RNA polymerase.

22. The method of claim 20 wherein the RNA polymerase promoter is selected from the group consisting of a promoter for T7 RNA polymerase, T3 RNA polymerase and SP6 RNA polymerase.

23. The method of claim 6 wherein an RNA polymerase for said transcription uses an RNA polymerase promoter encoded by a nucleic acid sequence from said target nucleic acid contained in said amplification product.

24. The method of claim 2 wherein said generating a directionally truncated polypeptide in said host cell comprises translation using a ribosome binding site and translation start signal encoded by nucleic acid sequences in said transposon contained in said replicated circular amplification product.

25. The method of claim 2 wherein said generating a directionally truncated polypeptide in said host cell comprises translation using a ribosome binding site and translation start signal encoded by nucleic acid sequences from said target nucleic acid contained in said replicated circular amplification product.

26. The method of claim 2 wherein said generating a directionally truncated polypeptide in said host cell comprises translation using a ribosome binding site and a translation start signal encoded by nucleic acid sequences in a primer used for said amplifying.

27. The method according to claim 5 wherein the selectable marker encodes at least one gene that is expressible in the host cell and, whereby, expression of the gene results in greater resistance of the host cell to toxicity of a chemical substance.

28. The method of claim 27 wherein the selectable marker is selected from the group consisting of genes for resistance to penicillin, ampicillin, kanamycin, neomycin, tetracycline, chloramphenicol, and trimethoprim.

29. The method of claim 1 wherein the transposon comprises end sequences that are recognized for transposition by a transposase selected from the group consisting of a wild-type or mutant form of a Tn5-type transposase, MuA-type transposase, Tn552-type transposase, Ty1-type transposase, Tn7-type transposase, Tn10-type transposase or IS10-type transposase, Tc1-type transposase, Tn3-type transposase, a P-element-type transposase, a Mariner-type transposase, and a Sleeping Beauty-type transposase.

30. The method of claim 1 wherein the origin of replication (ori) comprises fewer than about 300 to about 1000 nucleotides.

31. The method of claim 1 wherein the origin of replication (ori) is selected from the group consisting of a colE1-type ori, an R6Kγ-type ori, a p15Aori, and oriV.

32. The method of claim 1, wherein the second primer comprises translation stop codons for all three reading frames.

33. The method of claim 32, wherein said stop codons are positioned within the transposon end sequences or near to the left transposon end so that translation is terminated near to the amino-terminus of carboxyl-truncated polypeptides obtained.

34. The method of claim 4 wherein said bidirectionally-truncated polypeptide is obtained by:
(g) obtaining a first circular amplification product that was replicated in a host cell selected in step (f);
(h) inserting a second transposon into said first circular amplification product obtained in step (g) to generate first circular amplification products containing the second transposon;
(i) amplifying said first circular amplification products containing the second transposon by PCR using a forward primer that anneals to a sequence exhibited by the first circular amplification product and a reverse primer that anneals to the second transposon to generate second amplification products, each comprising a bidirectionally-truncated target nucleic acid;
(j) ligating said second amplification products so that each second amplification product is ligated to itself to generate a second circular amplification product;
(k) transforming said second circular amplification products into host cells, wherein said second circular amplification products are replicated;
(l) selecting a host cell that contains a second circular amplification product from among the host cells transformed in step (K), each of which contains a replicated second circular amplification product, wherein said selected host cell is used for generating said bidirectionally truncated polypeptide.

35. The method of claim 34 wherein a transposon end sequence recognized by a second transposase is used in step (h) in place of said second transposon.

36. The method of claim 35, wherein said transposon end sequence is a Mu-end transposon end and the second transposase is a wild-type or mutant MuA transposase.

37. The method of claim 34 wherein the same transposase is used in step (b) and (h).

38. The method of claim 37 wherein the transposase is a wild-type or mutant MuA transposase.

39. The method of claim 35 wherein the second transposase used in step (h) is different from the transposase used in step (b).

40. The method of claim 1, wherein said target nucleic acid comprises double-stranded DNA selected from among: genomes of bacteria, yeasts, viruses, viroids, mycoplasma, molds, microorganisms, fungi, plants, animals, and humans; chromosomes; mitochondrial DNA, chloroplast DNA, episomal DNA; and DNA made by reverse transcription of RNA.

* * * * *

UNITED STATES PATENT AND TRADEMARK OFFICE
CERTIFICATE OF CORRECTION

PATENT NO. : 7,727,744 B2  Page 1 of 1
APPLICATION NO. : 11/093387
DATED : June 1, 2010
INVENTOR(S) : Michael J. Fiandt and Gary A. Dahl It is certified that error appears in the above-identified patent and that said Letters Patent is hereby corrected as shown below:

Col. 33, Claim 11, Lines 2-4 should read as follows: "an expressible gene for T7-type RNA polymerase and the step of generating a directionally truncated polypeptide in said host cell comprises inducing said T7-type RNA polymerase in said host cells."

Signed and Sealed this

Sixth Day of July, 2010

David J. Kappos
*Director of the United States Patent and Trademark Office*